United States Patent
Zhou et al.

(10) Patent No.: US 10,695,735 B2
(45) Date of Patent: *Jun. 30, 2020

(54) PROBE INVERSION PROCESS FOR IN SITU SYNTHESIZED PROBE ARRAYS

(71) Applicant: Centrillion Technology Holdings Corporation, Grand Cayman (KY)

(72) Inventors: Wei Zhou, Saratoga, CA (US); Glenn McGall, Palo Alto, CA (US); Vijay Singh, Mountain View, CA (US)

(73) Assignee: Centrillion Technology Holdings Corporation, Grand Cayman (KY)

( * ) Notice: Subject to any disclaimer, the term of this patent is extended or adjusted under 35 U.S.C. 154(b) by 184 days.

This patent is subject to a terminal disclaimer.

(21) Appl. No.: 15/240,114

(22) Filed: Aug. 18, 2016

(65) Prior Publication Data

US 2017/0050162 A1 Feb. 23, 2017

Related U.S. Application Data

(60) Provisional application No. 62/206,741, filed on Aug. 18, 2015, provisional application No. 62/293,303, filed on Feb. 9, 2016.

(51) Int. Cl.
   *C07H 21/00* (2006.01)
   *B01J 19/00* (2006.01)
   *C40B 80/00* (2006.01)
   *C12Q 1/68* (2018.01)

(52) U.S. Cl.
   CPC ........... *B01J 19/0046* (2013.01); *C40B 80/00* (2013.01); *B01J 2219/00596* (2013.01); *B01J 2219/00608* (2013.01); *B01J 2219/00612* (2013.01); *B01J 2219/00626* (2013.01); *B01J 2219/00637* (2013.01); *B01J 2219/00641* (2013.01); *B01J 2219/00675* (2013.01); *B01J 2219/00711* (2013.01); *B01J 2219/00722* (2013.01); *C12Q 1/68* (2013.01)

(58) Field of Classification Search
   None
   See application file for complete search history.

(56) References Cited

U.S. PATENT DOCUMENTS

| | | | |
|---|---|---|---|
| 4,910,300 A * | 3/1990 | Urdea | C07H 21/00 435/6.12 |
| 5,242,974 A | 9/1993 | Holmes | |
| 5,959,098 A | 9/1999 | Goldberg et al. | |
| 6,077,608 A | 6/2000 | Barkac et al. | |
| 6,262,216 B1 | 7/2001 | McGall | |
| 6,835,827 B2 | 12/2004 | Vinayak et al. | |
| 8,105,821 B2 | 1/2012 | McGall et al. | |
| 9,328,382 B2 | 5/2016 | Drmanac et al. | |
| 2002/0051994 A1 | 5/2002 | Kwiatkowski et al. | |
| 2004/0152905 A1 | 8/2004 | Guzaev et al. | |
| 2007/0037175 A1 | 2/2007 | Leproust et al. | |
| 2008/0305964 A1 | 12/2008 | Bar-Ziv et al. | |
| 2010/0261181 A1 | 10/2010 | Agnew et al. | |
| 2011/0223585 A1 | 9/2011 | Gullberg et al. | |
| 2012/0035115 A1 | 2/2012 | Manoharan et al. | |
| 2012/0083417 A1 | 4/2012 | Zhou et al. | |
| 2013/0165350 A1 | 6/2013 | Kuimelis et al. | |
| 2013/0237459 A1 | 9/2013 | Rasmussen | |
| 2014/0186940 A1 | 7/2014 | Goel | |
| 2016/0046985 A1 | 2/2016 | Drmanac et al. | |
| 2016/0168632 A1 | 6/2016 | Edwards | |
| 2017/0022554 A1 | 1/2017 | Drmanac et al. | |

FOREIGN PATENT DOCUMENTS

| | | |
|---|---|---|
| CN | 102702010 A | 10/2012 |
| CN | 103502218 A | 1/2014 |
| WO | WO-9851698 A1 | 11/1998 |
| WO | WO-2011106460 A2 | 9/2011 |
| WO | WO-2012106546 A2 | 8/2012 |
| WO | WO-2011106460 A3 | 2/2013 |
| WO | WO-2012106546 A3 | 11/2013 |
| WO | WO-2015017759 A1 | 2/2015 |
| WO | WO-2015179790 A1 | 11/2015 |
| WO | WO-2017031278 A1 | 2/2017 |
| WO | WO-2018102660 | 6/2018 |

OTHER PUBLICATIONS

Briggs et al. Iterative capped assembly: rapid and scalable synthesis of repeat-module DNA such as TAL effectors from individual monomers, Nucleic Acids Research, vol. 40, Issue 15, Aug. 1, 2012, p. e117, https://doi.org/10.1093/nar/gks624.*
Ellington et al. "Synthesis and purification of oligonucleotides." Current Protocols in Molecular Biology 42.1 (1998): 2-11.*
Beaucage S.L. Strategies in the preparation of DNA oligonucleotide arrays for diagnostic applications. Curr. Med. Chem. Aug. 2001; 8(10): 1213-44.
"Beier, M et al. Production by the quantitative photolithographic synthesis of individually quality checked DNA microarrays. Nucleic Acid Research, vol. 28, No. 4, 2000, e11, pp. 1-6;".
Brown T, et al. Solid-phase oligonucleotide synthesis. [Online] Southampton, UK, ATDBio. http://www.atdbio.com/content/17/Solid-phase-oligonucleotide-synthesis [Accessed Aug. 9, 2016].
Chow B.Y., et al. Photoelectrochemical synthesis of DNA microarrays. Proc Natl Acad Sci USA 2009, 106, 15219-24.
Co-pending U.S. Appl. No. 15/305,213, filed Oct. 19, 2016.

(Continued)

*Primary Examiner* — Patrick T Lewis
(74) *Attorney, Agent, or Firm* — Wilson Sonsini Goodrich & Rosati

(57) ABSTRACT

The present disclosure relates to processes for inverting oligonucleotide probes in an in situ synthesized array. These processes can be used to reverse the orientation of probes with respect to the substrate from 3'-bound to 5'-bound. These processes can also be used to reduce or eliminate the presence of truncated probe sequences from an in situ synthesized array.

19 Claims, 23 Drawing Sheets

Specification includes a Sequence Listing.

(56) References Cited

OTHER PUBLICATIONS

Lindroos, et al. Minisequencing on oligonucleotide microarrays: comparison of immobilisation chemistries. Nucleic Acids Res. Jul. 1, 2001; 29(13): e69.
Forman, et al., Molecular Modeling of Nucleic Acids, Chapter 13, p. 221, American Chemical Society (1998).
Hughes T. R., et al. Expression profiling using microarrays fabricated by an ink-jet oligonucleotide synthesizer. Nature Biotechnol 2001, 19, 342-7.
International search report and written opinion dated Aug. 19, 2015 for PCT Application No. PCT/US2015/032227.
"International search report with written opinion dated Oct. 31, 2016 for PCT/US16/47488".
Kool Eric T., Versatile 5'—Functionalization of Oligonucleotides on Solid Support: Amines, Azides, Thiols, and Thioethers via Phosphorus Chemistry. J Org. Chem. 2004, 69, 2404-2410.
Kumar, et al. Template-Directed Oligonucleotide Strand Ligation, Covalent Intramolecular DNA Circularization and Catenation Using Click Chemistry. JACS, 2007, 129(21), 6859.
Lausted C., et al. POSaM: a fast, flexible, open-source, inkjet oligonucleotide synthesizer and microarrayer.Genome Biol 2004, 5, R58.
"Markiewicz, WT et al. A new method of synthesis of fluorescently labelled oligonucleotides and their application in DNA sequencing. Nucleic Acids Research, vol. 25, No. 18, 1997, pp. 3672-3680".
Marshall et al. DNA chips: an array of possibilities. Nat. Biotechnol. Jan. 1998; 16:27-31.
Maurer, et al. Electrochemically Generated Acid and Its Containment to 100 Micron Reaction Areas for the Production of DNA Microarrays. PLoS One. 2006; 1(1): e34.
McGall, et al. Light-directed synthesis of high-density oligonucleotide arrays using semiconductor photoresists. Proc Natl Acad Sci USA 1996; 93:13555-60.
McGall G., et al. The efficiency of light-directed synthesis of DNA arrays on glass substrates J. Am. Chem. Soc. 119:5081-5090 (1997).
McGall G. H., et al. Photolithographic synthesis of arrays. In Methods in Molecular Biology: DNA Arrays, Methods and Protocols; J.B. Rampal, Ed.; Humana Press: Torowa, NJ, 2001; vol. 170, 71-101.
Pawloski A.R., et al. Photolithographic synthesis of high-density DNA probe arrays : Challenges and opportunities. J Vac Sci Technol B 2007, 25, 2537-46.
Pease A.C., et al. Light-generated oligonucleotide arrays for rapid DNA sequence analysis. Proc Natl Acad Sci USA 1994, 91, 5022-6.
Schena M. DNA Microarrays: A Practical Approach (Practical Approach Series). Oxford University Press. 1st edition.
Shelbourne et al. Fast copper-free click DNA ligation by the ring-strain promoted alkyne-azide cycloaddition reaction. Chem. Commun., 2011, 47:6257-6259.
Singh-Gasson S., et al. Maskless fabrication of light-directed oligonucleotide microarrays using a digital micromirror array.Nature Biotechnol 1999, 17, 974-8.
Spitale RC, et al. Structural imprints in vivo decode RNA regulatory mechanisms. Nature, 2015, 519(7544):486-90.
Gunderson, et al. A genome-wide scalable SNP genotyping assay using microarray technology. Nat Genet 37:549-554.
Extended European Search Report and Search Opinion dated Oct. 19, 2017 for European Patent Application No. 15796731.6.
Kwiatkowski, et al., Inversion of in situ synthesized oligonucleotides; improved reagents for hybridization and primer extension in DNA microarrays, Nucleic Acids Research, Information Retrieval Ltd, Jan. 1, 1999, 27(24):4710-14.
Glen Research Corporation, Catalog 2011.
PCT/US2016/047488 International Preliminary Report on Patentability dated Mar. 1, 2018.
PCT/US2017/064169 International Search Report and Written Opinion dated Mar. 7, 2018.
CN2015800273478 Office Action dated May 23, 2018 (w/ English translation).
EP15796731.6 Extended Search Report dated Oct. 19, 2017.
EP16184815.5 Extended Search Report dated Jan. 2, 2017.
Horn et al. Chemical synthesis and characterization of branched oligodeoxyribonucleotides (bDNA) for use as signal amplifiers in nucleic acid quantification assays. Nucleic Acids Research 25(23):4842-4849 (Jan. 1, 1997).
PCT/US2015/032227 International Preliminary Report on Patentability dated Nov. 29, 2016.
PCT/US2016/047488 International Preliminary Report on Patentability dated Feb. 20, 2018.
U.S. Appl. No. 15/305,213 Office Action dated Jun. 15, 2018.
U.S. Appl. No. 15/305,213 Final Office Action dated Jun. 4, 2019.

* cited by examiner

PROBE INVERSION PROCESS FOR IN SITU SYNTHESIZED PROBE ARRAYS

CROSS-REFERENCE

This application claims the benefit of U.S. Provisional Application No. 62/206,741, filed Aug. 18, 2015 and U.S. Provisional Application No. 62/293,203, filed Feb. 9, 2016, which applications are incorporated herein by reference.

SEQUENCE LISTING

The instant application contains a Sequence Listing which has been submitted electronically in ASCII format and is hereby incorporated by reference in its entirety. Said ASCII copy, created on Aug. 16, 2016, is named 38558-711_201_SL.txt and is 1,906 bytes in size.

BACKGROUND

The synthesis of oligonucleotide probes on in situ synthesized arrays, such as by photolithography, can result in a population of incomplete or truncated probe sequences which accompany the probe sequences synthesized at the full desired or intended length ("full-length" probes). The presence of such truncated probe sequences can have a detrimental effect on array performance, especially in arrays requiring enzymatic addressing of the free probe terminus, such as polymerase extension reactions or ligation reactions.

In contrast, oligonucleotide probes immobilized on bead arrays (e.g., Illumina) and other spotted arrays are commonly attached to their substrates via an amine or other functional group synthetically attached to the 5' end of the probe. In this way, only full-length sequences are immobilized, and truncations or other defects associated with an exposed free 3' end are reduced or virtually eliminated.

SUMMARY

It can be desirable to selectively remove truncated probe sequences post-synthesis from among the probes on in situ synthesized arrays, such as those fabricated with photolithography. The present disclosure provides processes for accomplishing this selective removal of truncated sequences, while simultaneously inverting the orientation of the probe sequence such that probe sequences synthesized from the 3'-end are converted to probe sequences attached to the substrate via their 5'-end.

In particular, this disclosure includes probe inversion processes for in situ synthesized arrays which can use universal linkers and commercially available building blocks and reagents. These can include incorporation of a universal cleavable linker phosphoramidite for use in releasing free 3'-OH termini, incorporation of branched linkers with orthogonally protected, addressable functional groups for oligonucleotide synthesis and post-synthesis circularization, more efficient crosslinking chemistries for circularization steps utilizing commercially available reagents, and other improvements. Previous processes attempting probe inversion on in situ synthesized arrays involved a large number of special linkers, building blocks and reagents, which can make it impractical to use for large scale manufacturing of in situ synthesized arrays.

An aspect of the present disclosure provides a method, comprising: providing a substrate with a plurality of branched linkers coupled to said substrate, wherein said substrate comprises a plurality of hydroxyalkyl groups, wherein each branched linker comprises (i) a first branch comprising a first alkyne and (ii) a second branch, wherein said second branch comprises a first cleavable linker coupled to a 3' end of a first oligonucleotide, and wherein a 5' end of said first oligonucleotide is coupled to a first azide group; and circularizing said first oligonucleotide by reacting said first azide group with a second alkyne, wherein said second alkyne is said first alkyne or a neighboring alkyne; wherein efficiency of said circularization increases when said second branch further comprises a capping moiety.

In some embodiments of aspects provided herein, said plurality of branched linkers are coupled to said substrate via said plurality of hydroxyalkyl groups. In some embodiments of aspects provided herein, said plurality of branched linkers coupled to said substrate via a first intermediate selected from the group consisting of the structures shown in FIG. 2A, FIG. 2B, and FIG. 2C. In some embodiments of aspects provided herein, said second alkyne is said first alkyne. In some embodiments of aspects provided herein, said first cleavable linker becomes part of said branched linker via a second intermediate selected from the group consisting of the structures shown in FIG. 3A, FIG. 3B, and FIG. 3C. In some embodiments of aspects provided herein, the ratio between said cleavable linker and said first alkyne is about 5, about 4, about 3, about 2, about 1, about 0.5, about 0.33, about 0.25, about 0.2, or about 0.1. The method of claim 1, the method further comprises (c) cleaving said first cleavable linker, thereby decoupling said 3' end of said first oligonucleotide from said second branch. In some embodiments of aspects provided herein, said cleaving comprises de-protection with a base. In some embodiments of aspects provided herein, said said efficiency is at least 70%, at least 80%, at least 90%, or at least 95%. In some embodiments of aspects provided herein, another second branch comprises a second cleavable linker coupled to a 3' end of a second oligonucleotide, wherein said second oligonucleotide is shorter than said first oligonucleotide, and wherein said cleaving releases said second oligonucleotide from said substrate. In some embodiments of aspects provided herein, said cleaving releases at least 90% of said second oligonucleotide from said substrate.

Another aspect of the present disclosure provides a method, comprising: providing a substrate; attaching a plurality of branched linkers to said substrate, wherein said branched linkers comprise (i) a first branch comprising an alkyne and (ii) a second branch; attaching a cleavable linker to a first group of said second branches; attaching a capping moiety to a second group of said second branches; synthesizing a first oligonucleotide on said cleavable linker in 3' to 5' orientation, said first oligonucleotide comprising (i) a 3' end coupled to said second branch via said cleavable linker and (ii) a 5' end coupled to an azide group; and circularizing said first oligonucleotide by reacting said azide group with said alkyne, thereby coupling said 5' end of said first oligonucleotide to one of said first branches.

In some embodiments of aspects provided herein, the ratio of said first group of second branches to said second group of second branches is between about 5:1 to about 1:5. In some embodiments of aspects provided herein, the ratio of said first group of second branches to said second group of second branches is about 5:1, about 4:1, about 3:1, about 2:1, about 1:1, about 1:2, about 1:3, about 1:4, or about 1:5. In some embodiments of aspects provided herein, the ratio of said first group of second branches to said second group of second branches is about 1 or less. In some embodiments of aspects provided herein, wherein said capping moiety is attached via an intermediate of capping phosphoramidite. In some embodiments of aspects provided herein, said substrate comprises a plurality of hydroxyalkyl groups. In some embodiments of aspects provided herein, said branched linker is coupled to said substrate via said plurality of hydroxyalkyl groups. In some embodiments of aspects provided herein, the method further comprises (c) cleaving said cleavable linker, thereby de-coupling said 3' end of said first oligonucleotide from said first group of said second branch. In some embodiments of aspects provided herein, a second oligonucleotide is attached to a third group of said second branch, wherein said second oligonucleotide lacks a covalent bond to said first branch, wherein said cleaving releases said second oligonucleotide from said substrate. In some embodiments of aspects provided herein, the substrate comprises controlled core glass. In some embodiments of aspects provided herein, said synthesizing comprises photolithographic synthesis.

Another aspect of the present disclosure provides a system, comprising: a substrate comprising a plurality of hydroxyalkyl groups; and a plurality of branched linkers coupled to said plurality of hydroxyalkyl groups, wherein each said branched linker comprises (i) a first branch comprising a first alkyne and (ii) a second branch, wherein said second branch comprises a first cleavable linker and a capping moiety, wherein said first cleavable linker is coupled to a 3' end of a first oligonucleotide, and wherein a 5' end of said first oligonucleotide is coupled to a first azide group.

In some embodiments of aspects provided herein, said first azide group reacts with a second alkyne to circularize said first oligonucleotide, wherein said second alkyne is said first alkyne or a neighboring alkyne. In some embodiments of aspects provided herein, the ratio between said cleavable linker and said capping moiety is about 10, about 5, about 4, about 3, about 2, about 1, about 0.5, about 0.33, about 0.25, about 0.2, or about 0.1. In some embodiments of aspects provided herein, said plurality of branched linkers coupled to said substrate via a first intermediate selected from the group consisting of the structures shown in FIG. 2A, FIG. 2B, and FIG. 2C. In some embodiments of aspects provided herein, said first cleavable linker becomes part of said branched linker via a second intermediate selected from the group consisting of the structures shown in FIG. 3A, FIG. 3B, and FIG. 3C. In some embodiments of aspects provided herein, said capping moiety is acyl, dialkoxyphosphoryl, alkyl, alkoxycarbonyl, or dialkyaminocarbonyl. In some embodiments of aspects provided herein, said first cleavable linker is cleavable by with a base, for example, ammonia, methyl amine, 1,2-diaminoethane, and potassium carbonate.

Another aspect of the present disclosure provides a method, comprising: providing a substrate with a plurality of branched linkers coupled to said substrate, wherein each branched linker comprises (i) a first branch comprising a first alkyne and (ii) a second branch, wherein said second branch comprises a cleavable linker coupled to a 3' end of a first oligonucleotide, and wherein a 5' end of said first oligonucleotide is coupled to an azide group; reacting said azide group with a second alkyne to circularize said first oligonucleotide, said reaction being catalyzed by a Cu(I) catalyst in a buffer at room temperature, said second alkyne being said first alkyne or a neighboring alkyne; and (c) cleaving said cleavable linker, thereby inverting said first oligonucleotide.

In some embodiments of aspects provided herein, said second alkyne is said first alkyne. In some embodiments of aspects provided herein, the method further comprises: (d) providing a second oligonucleotide complementary to at least part of inverted first oligonucleotide obtained in (c), wherein said second oligonucleotide leaves a 3' overhang after hybridization with said inverted first oligonucleotide; and (e) extending said second oligonucleotide with a polymerase and fluorescently labeled dNTP, thereby confirming said inversion of said first oligonucleotide.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12A shows an image of incorporation of dGTP nucleotides at 3' postion of inverted wafer chip in a single-base extension.

FIG. 12B shows an image of incorporation of dTTP nucleotides at 3' position of inverted wafer chip in a single-base extension (inset: enlarged portion of actual image showing array features).

FIG. 12C shows an image of incorporation of dATP nucleotides at 3' position of inverted wafer chip in a single-base extension.

FIG. 12D shows an image of incorporation of dCTP nucleotides at 3' position of inverted wafer chip in a single-base extension.

DETAILED DESCRIPTION

Figure 1A:
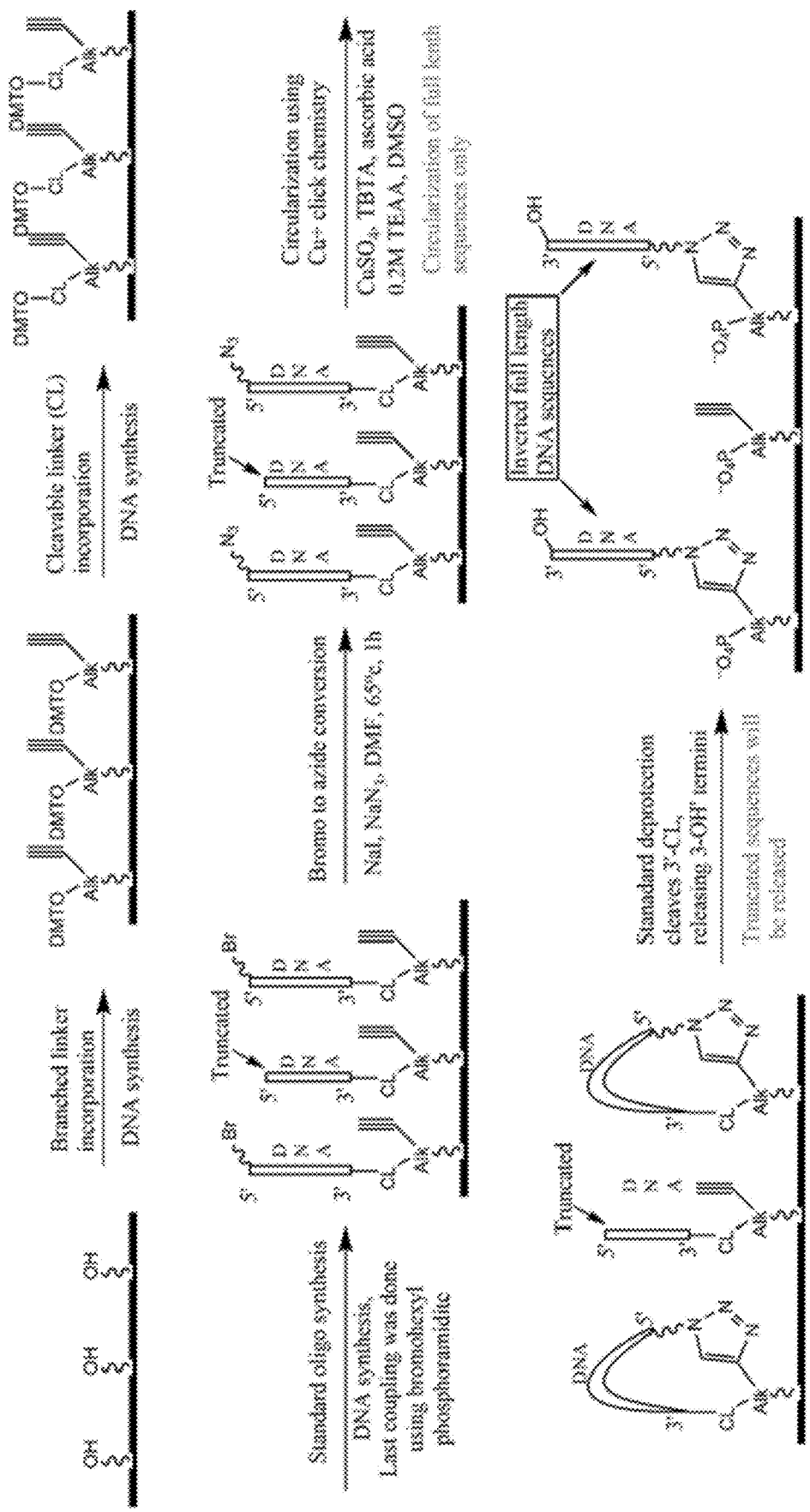
FIG. 1A shows an exemplary process for inverting a probe.

The present disclosure provides processes for the circularization and inversion of in situ synthesized oligonucleotide probes. Particular circularization chemistries are described, including click chemistry reactions using bromo or iodide groups. Such reactions can be used to bind the 5' ends of oligonucleotides to surface-bound linker molecules; circularized oligonucleotides can then have their 3' ends released, thereby inverting the oligonucleotides. The processes disclosed herein can also reduce or eliminate truncated oligonucleotide probes, which do not contain the full synthesized oligonucleotide sequence, while preserving full-length oligonucleotide probes, which do contain the full synthesized oligonucleotide sequence. For example, full-length oligonucleotides can be circularized prior to release of the 3' ends, while non-full-length oligonucleotides remain un-circularized and therefore are removed from the surface upon release of the 3' ends.

The term "oligonucleotide" can refer to a nucleotide chain. In some cases, an oligonucleotide is less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "click chemistry" can refer to reactions that are modular, wide in scope, give high yields, generate only inoffensive byproducts, such as those that can be removed by nonchromatographic methods, and are stereospecific (but not necessarily enantioselective). An exemplary click chemistry reaction is the Huisgen 1,3-dipolar cycloaddition of an azide and an alkynes, i.e., Copper-catalyzed reaction of an azide with an alkyne to form a 5-membered heteroatom ring, known as a Cu(I)-Catalyzed Azide-Alkyne Cycloaddition (CuAAC).

The term "click chemistry moiety" can be a terminal alkyne.

The term "about" as used herein refers to +/−10%, 9%, 8%, 7%, 6%, 5%, 4%, 3%, 2%, or 1% of the designated amount.

The term "circularize" or "circularization" as used herein refers to the structure of an oligonucleotide with both of its ends attached to the substrate or support via covalent bonds.

Genetic information can be utilized in a myriad of ways with the advent of rapid genome sequencing and large genome databases. One of such applications is oligonucleotide arrays. The general structure of an oligonucleotide array, or commonly referred to as a DNA microarray or DNA array or a DNA chip, is a well-defined array of spots or addressable locations on a surface. Each spot can contain a layer of relatively short strands of DNA called "probe" or "capture probe" (e.g., Schena, ed., "DNA Microarrays A Practical Approach," Oxford University Press; Marshall et al. (1998) *Nat. Biotechnol.* 16:27-31; each incorporated herein by reference). There are at least two technologies for generating arrays. One is based on photolithography (e.g. Affymetrix) while the other is based on robot-controlled ink jet (spotbot) technology (e.g., Arrayit.com). Other methods for generating microarrays are known and any such known method may be used herein.

Generally, an oligonucleotide (probe or capture probe) placed within a given spot in the array is selected to bind at least a portion of a nucleic acid or complimentary nucleic acid of a target nucleic acid. An aqueous sample is placed in contact with the array under the appropriate hybridization conditions. The array is then washed thoroughly to remove all non-specific adsorbed species. In order to determine whether or not the target sequence was captured, the array can be "developed" by adding, for example, a fluorescently labeled oligonucleotide sequence that is complimentary to an unoccupied portion of the target sequence. The microarray is then "read" using a microarray reader or scanner, which outputs an image of the array. Spots that exhibit strong fluorescence are positive for that particular target sequence.

A probe can comprise biological materials deposited so as to create spotted arrays. A probe can comprise materials synthesized, deposited, or positioned to form arrays according to other technologies. Thus, microarrays formed in accordance with any of these technologies may be referred to generally and collectively hereafter for convenience as "probe arrays." The term "probe" is not limited to probes immobilized in array format. Rather, the functions and methods described herein can also be employed with respect to other parallel assay devices. For example, these functions and methods may be applied when probes are immobilized on or in beads, optical fibers, or other substrates or media.

In methods and systems of the present disclosure, probes can be attached to a solid substrate. Probes can be bound to a substrate directly or via a linker. Linkers can comprise, for example, amino acids, polypeptides, nucleotides, oligonucleotides, or other organic molecules that do not interfere with the functions of probes.

The solid substrate can be biological, non-biological, organic, inorganic, or a combination of any of these. The substrate can exist as one or more particles, strands, precipitates, gels, sheets, tubing, spheres, containers, capillaries, pads, slices, films, plates, slides, or semiconductor integrated chips, for example. The solid substrate is can be flat or can take on alternative surface configurations. For example, the solid substrate can contain raised or depressed regions on which synthesis or deposition takes place. In some examples, the solid substrate can be chosen to provide appropriate light-absorbing characteristics. For example, the substrate can be a polymerized Langmuir Blodgett film, functionalized glass (e.g., controlled pore glass), silica, titanium oxide, aluminum oxide, indium tin oxide (ITO), Si, Ge, GaAs, GaP, $SiO_2$, $SiN_4$, modified silicon, the top dielectric layer of a semiconductor integrated circuit (IC) chip, or any one of a variety of gels or polymers such as (poly) tetrafluoroethylene, (poly)vinylidenedifluoride, polystyrene, polycarbonate, polydimethylsiloxane (PDMS), polymethylmethacrylate (PMMA), polycyclicolefins, or combinations thereof.

Solid substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

DNA microarrays can be fabricated using spatially-directed in situ synthesis or immobilization of pre-synthesized oligonucleotides. In both cases, synthesis of the oligonucleotides typically proceeds with the addition of monomers in the 3'-to-5' direction, using standard 3'-phosphoramidite reagents and solid-phase synthesis protocols (e.g., M. Egli, et al., ed. "Current Protocols in Nucleic Acid Chemistry," John Wiley & Sons). The main impurities are truncated, partial-length sequences resulting from incomplete monomer coupling and, to a lesser extent, depurination reactions.

On the one hand, fabricating arrays of pre-synthesized oligonucleotide probes typically involves covalent attachment of the oligonucleotides to a substrate through the 5'-terminus, via a reactive modifier which is added to the end when the oligonucleotides are synthesized on high-throughput synthesizers (see S. J. Beaucage, et al., Curr. Med. Chem. 2001, 8, 1213-44). This ensures that the probes which are attached to the support are primarily full-length sequences, since truncated sequences are capped and rendered non-reactive during synthesis (Brown T and Brown T, Jr. (2005-2015) Solid-phase oligonucleotide synthesis. [Online] Southampton, UK, ATDBio. <http://www.atdbio.com/content/17/Solid-phase-oligonucleotide-synthesis> [Accessed Aug. 9, 2016]).

A significant advantage of the present disclosure is that the 3'-hydroxyl group of the oligonucleotide probe is "distal" to the substrate, and freely available for enzymatic reactions, such as template-directed polymerase-catalyzed chain extension and ligation; and this character can be exploited to carry out very sensitive and specific assays for detecting and quantitating genetic polymorphisms (K. Lindroos, et al., Nucleic Acids Res. 2001, 29, e69; Gunderson K L, et al., Nature Genetics 2005, 37, 549-54).

On the other hand, DNA microarrays can also be fabricated using in situ synthesis of sequences directly on the support. In this case, sequences are "printed" in a highly parallel fashion by spatially-directing the synthesis using inkjet (T. R. Hughes, et al., Nature Biotechnol 2001, 19, 342-7; C. Lausted, et al., Genome Biol 2004, 5, R58), photolithographic technologies (A. C. Pease, et al., Proc Natl Acad Sci USA 1994, 91, 5022-6; G. McGall, et al., Proc Natl Acad Sci USA 1996; 93:13555-60; S. Singh-Gasson, et al., Nature Biotechnol 1999, 17, 974-8;), or electrochemical techniques (PLoS ONE 2006, 1, e34; B. Y. Chow, et al., Proc Natl Acad Sci USA 2009, 106, 15219-24). Here too, synthesis proceeds 3' to 5' direction (solid-phase oligonucleotide synthesis in the 5'-to-3' direction, while feasible, is much less efficient and economical, providing lower yields and product purity). However, the resulting probes are attached to the substrate at the 3'-terminus, and any truncated sequence impurities which arise during the synthesis remain on the support, which may be a particular issue in the case of photolithographic synthesis (J. Forman, et al., Molecular Modeling of Nucleic Acids, Chapter 13, p. 221, American Chemical Society (1998) and G. McGall, et al., J. Am. Chem. Soc. 119:5081-5090 (1997)). As a result, polymerase-based extension assays normally are not feasible using arrays which are made this way.

Despite the above limitation, photolithographic synthesis is a highly attractive means of fabricating very high-density DNA arrays, as it is capable of exceeding 10 million arrayed sequences per $cm^2$ (A. R. Pawloski, et al., J Vac Sci Technol B 2007, 25, 2537-46), and is highly scalable in a manufacturing setting.

Thus, it is highly desirable to develop an effective method of inverting the sequences on such probe arrays.

The plurality of probes can be located in one or more addressable regions (spots, locations, etc.) on a solid substrate, herein referred to as "pixels." In some cases, a solid substrate comprises at least about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with probes. In some cases, a solid substrate comprises at most about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with probes. In some cases, a solid substrate comprises about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with probes.

In some cases it is useful to have pixels which do not contain probes. Such pixels can act as control spots in order to increase the quality of the measurement, for example, by using binding to the spot to estimate and correct for non-specific binding. In some cases, the density of the probes can be controlled to either facilitate the attachment of the probes or enhance the ensuing detection by the probes.

In some examples, it is useful to have redundant pixels which have identical probe sequences to another pixel but physically may not be adjacent or in proximity to the other pixel. The data acquired by such probe arrays may be less susceptible to fabrication non-idealities and measurement errors.

In some cases, labels are attached to the probes within the pixels, in addition to the labels that are incorporated into the targets. In such systems, captured targets can result in two labels coming into intimate proximity with each other in the pixel. As discussed before, interactions between specific labels can create unique detectable signals. For example, when the labels on the target and probe, respectively, are fluorescent donor and acceptor moieties that can participate in a fluorescent resonance energy transfer (FRET) phenomenon, FRET signal enhancement or signal quenching can be detected.

Synthesis of Inverted Oligonucleotides

FIG. 1A shows an exemplary process for inversion of probes in an in situ synthesized probe array and removal of truncated probe sequences. First, a synthesis substrate is prepared, comprising available surface groups such as hydroxyl groups, as shown in FIG. 1A. These hydroxyl groups are part of hydroxyalkyl groups on the synthesis substrate or support. For example, a surface may be modified with reagents, e.g., hydroxyalkyltrialkoxysilane, to provide hydroxyalkyl groups available for the branched liker to attach. Alternatively, a polymer thin film can be applied to the surface of the synthesis substrate or support, wherein the polymer contains free hydroxyl groups for attachment. Furthermore, a support that is compatible with DNA synthesis reagent and processing conditions and that contains hydroxyalkyl groups can be used for the attachment of the branched linker.

A branched linker (e.g., ALK, in FIG. 1B) can then be added to the surface of the synthesis substrate or support via all kinds of intermediates to introduce an alkyne on one position/branch and a DMT-protected hydroxyl group (to attach an oligonucleotide later) on another position/branch. The above-mentioned intermediates for the introduction of branched linkers include but are not limited to, a branched linker amidite intermediate (e.g., alkyne-modifier serinol phosphoramidite in FIG. 1B (left panel) and FIG. 2C), or intermediates as shown in FIG. 2A and FIG. 2B.

Figure 2A:
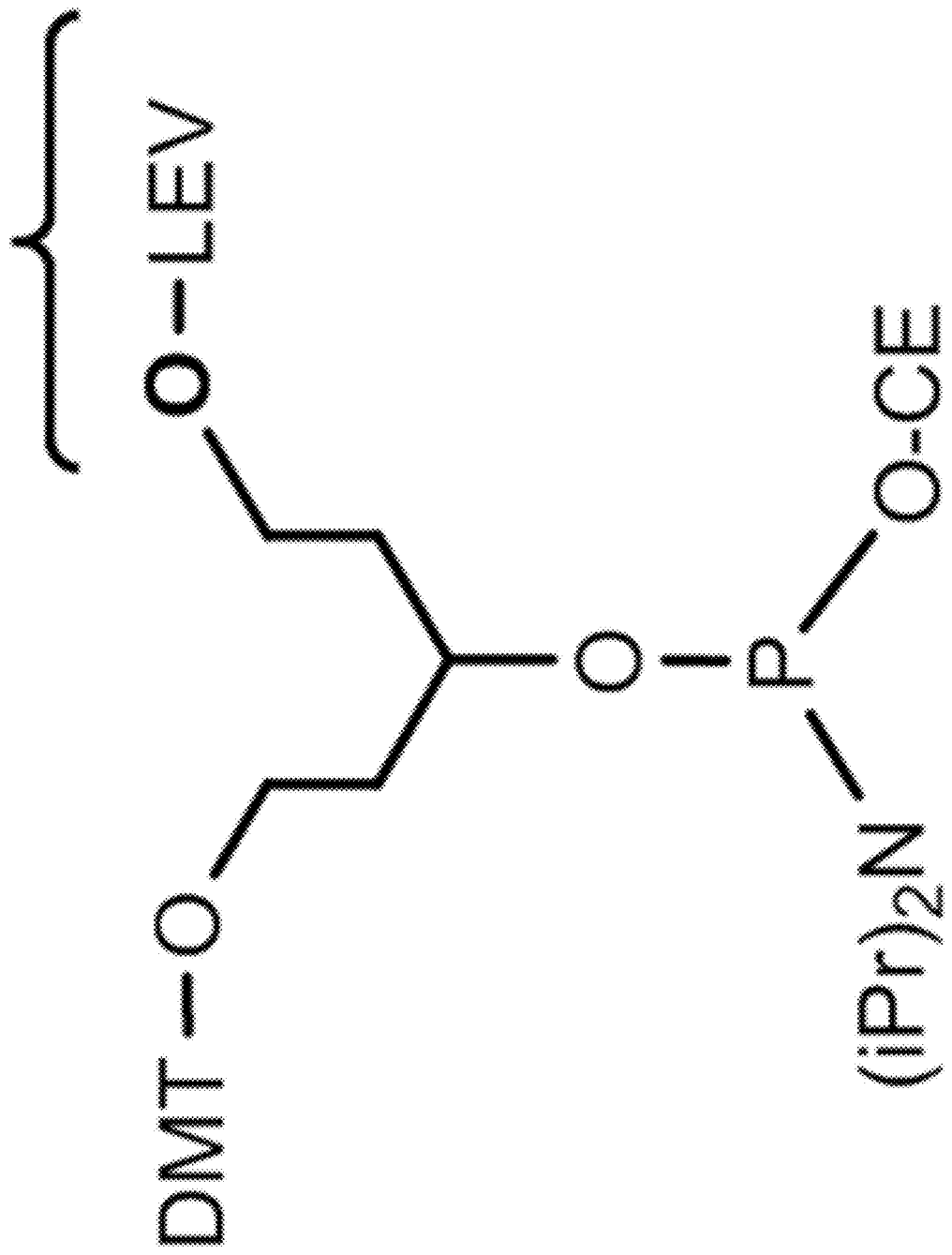
FIG. 2A shows an exemplary intermediate leading to branched linker.
Figure 2B:
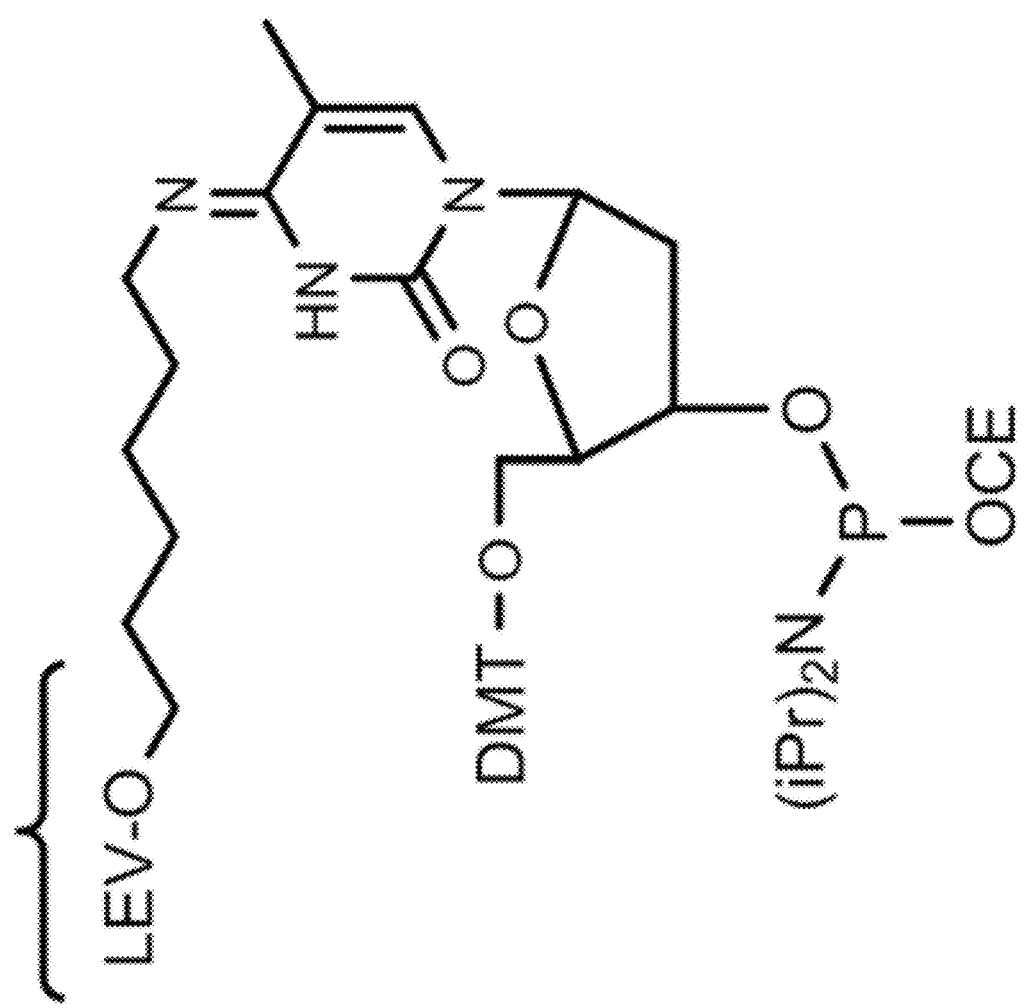
FIG. 2B shows an exemplary intermediate leading to branched linker.
Figure 2C:
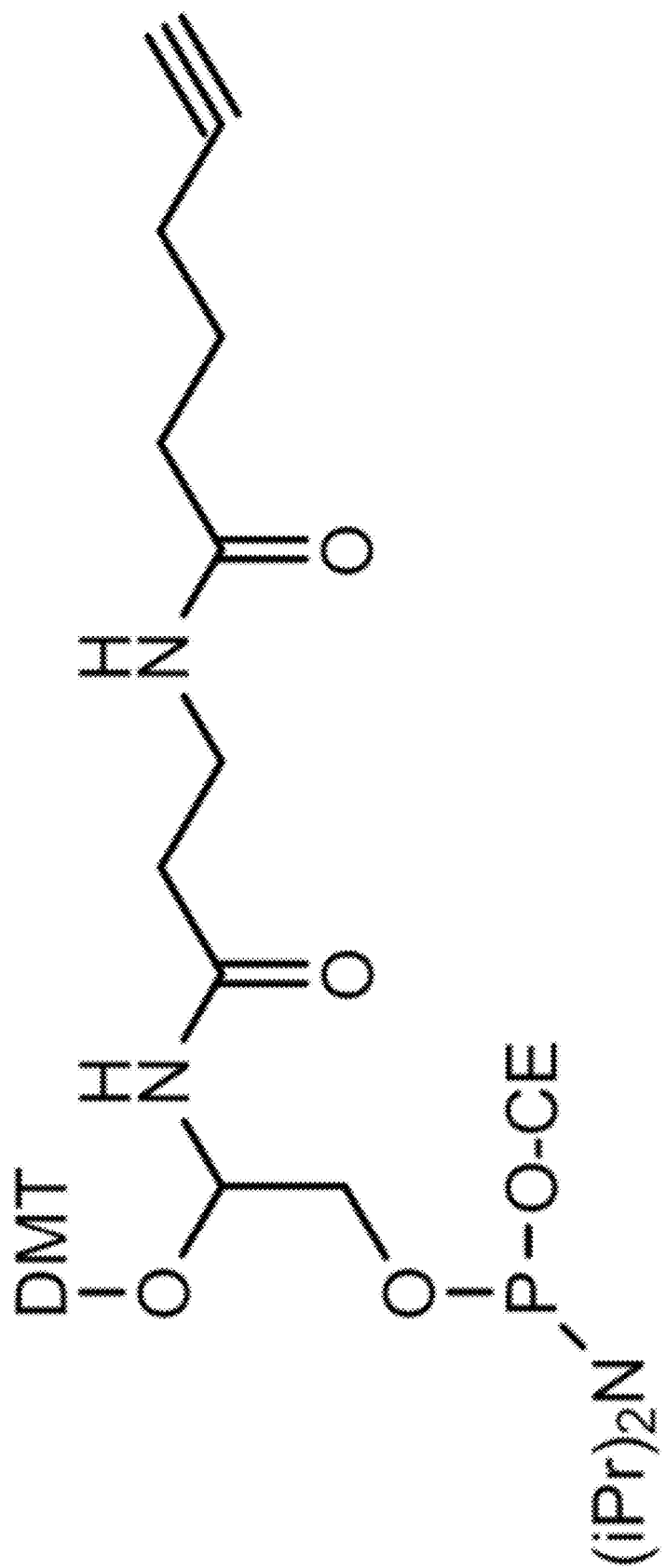
FIG. 2C shows an exemplary intermediate leading to branched linker.

Turning now to FIGS. 2A and 2B, levulinyl (LEV) is a protecting group for hydroxyl groups and can be specifically removed using a reagent containing hydrazine hydrate, acetic acid and pyridine (e.g., with 0.5 M hydrazine hydrate in 1:1 pyridine/acetic acid). 4,4'-Dimethoxytrityl (DMT) is another hydroxyl protecting group that can be removed under acidic conditions. 2-Cyanoethyl (CE) is a phosphite/phosphate protection and can be removed under basic conditions. The molecules shown in FIGS. 2A, 2B and 2C are commercially available from Glen Research (Sterling, Va. 20164).

Intermediates for the introduction of the branched linkers, for example, those shown in FIG. 2A and FIG. 2B, can not only react with surface hydroxyalkyl groups to attach to the support, but also have two orthogonally protected hydroxyl groups to allow the introduction of azide-attached oligonucleotide, alknyne, or a capping moiety. For example, a few additional steps are needed to attach an alkyne group to the first branch of the branched linker. First, phosphoramidite intermediates in FIG. 2A and FIG. 2B are coupled to the surface hydroxyalkyl groups on the support, followed by an oxidation of the resulting phosphite to phosphate. Then the LEV protection group is selectively removed without affecting the DMT protection group to reveal a hydroxyl group. An alkyne-containing phosphoramidite, for example, Compound A, is then coupled to the unmasked hydroxyl group to complete the synthesis of the first branch with an alkyne. Oxidation of the phosphite to phosphate can be carried out after the reaction of Compound A with the surface hydroxyalkyl groups.

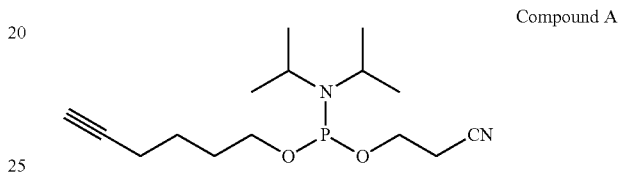

Compound A

Alternatively, alkyne-modifier serinol phosphoramidite in FIG. 2C can be coupled to the support directly. Because the alkyne group is preinstalled in this intermediate, no extra step is needed to introduce an alkyne group to the first branch.

After installation of the first branch containing an alkyne group, the DMT protection group can be removed to provide another hydroxyl group as a handle for the attachment of a cleavable linker, followed by the attachment of an oligonucleotide. Oligonucleotides can be introduced by any oligonucleotide synthesis method in a stepwise manner. For each round of oligonucleotide synthesis, a capping step is performed to cap a free hydroxyl group after the extension (no extension of the oligonucleotide chain on this free hydroxyl group) with an acetyl group or other suitable capping molecule after the phosphorylation. In this way capped failure sequences are prevented from participating in the rest of the chain elongation for the targeted oligonucleotide. Thus, these caped failure sequences are truncated oligonucleotides as shown in FIG. 1A. At the final step of the oligonucleotide chain extension, the unmasked 5' hydroxyl group of the last nucleic acid can be capped with an azide containing tail. This step can be achieved by first introducing a linker with a leaving group at the end. The leaving group can be Cl, Br, I, mesylate, tosylate, or triflate. Then replace the leaving group with an azide. An example of bromide to azide transformation is shown on the second row of FIG. 1A.

As described above, the linkers can comprise a post-synthesis reactive group, such as for click chemistry. For example, an alkyne group can be used, which can be stable during DNA synthesis of the oligonucleotides, and therefore would not require the use of protection/de-protection strategies. Branched linkers and cleavable inkers having phosphoramidite moieties, can be added to the synthesis substrate or support to provide access points for the later introduction of oligonucleotides using standard DNA synthesis protocols. In some cases, linkers can be added to the synthesis substrate using standard DNA synthesis protocols with extended coupling times (e.g., 3 minutes).

Figure 1B:
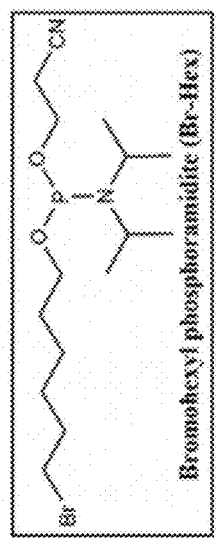
FIG. 1B shows exemplary intermediates for branched linker (left) and cleavable linker (center), and bromohexyl phosphoramidite (right).
Figure 1B:
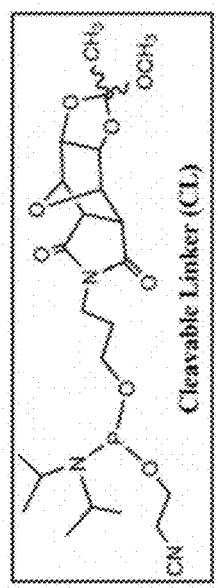
Figure 1B:
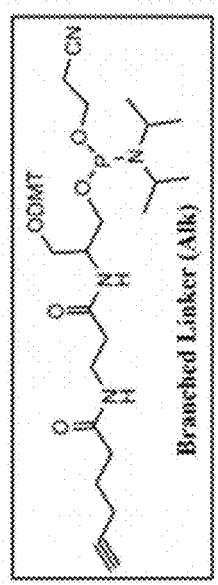
Figure 3A:
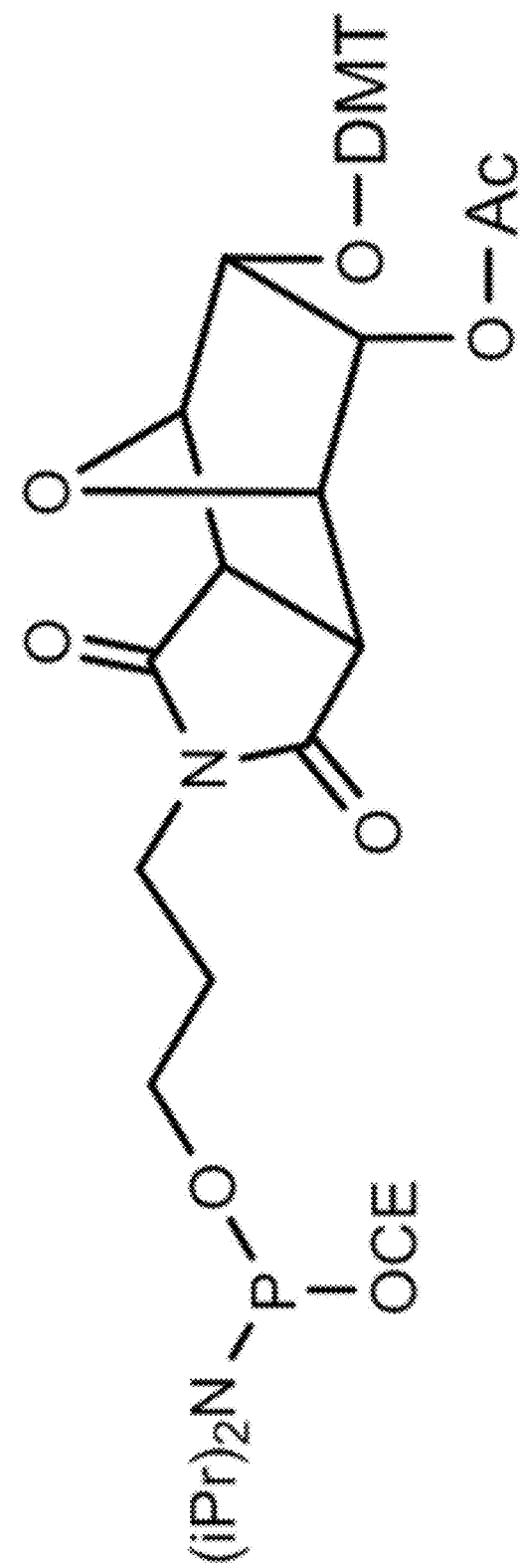
FIG. 3A shows an exemplary intermediates leading to cleavable linker (CL).
Figure 3B:
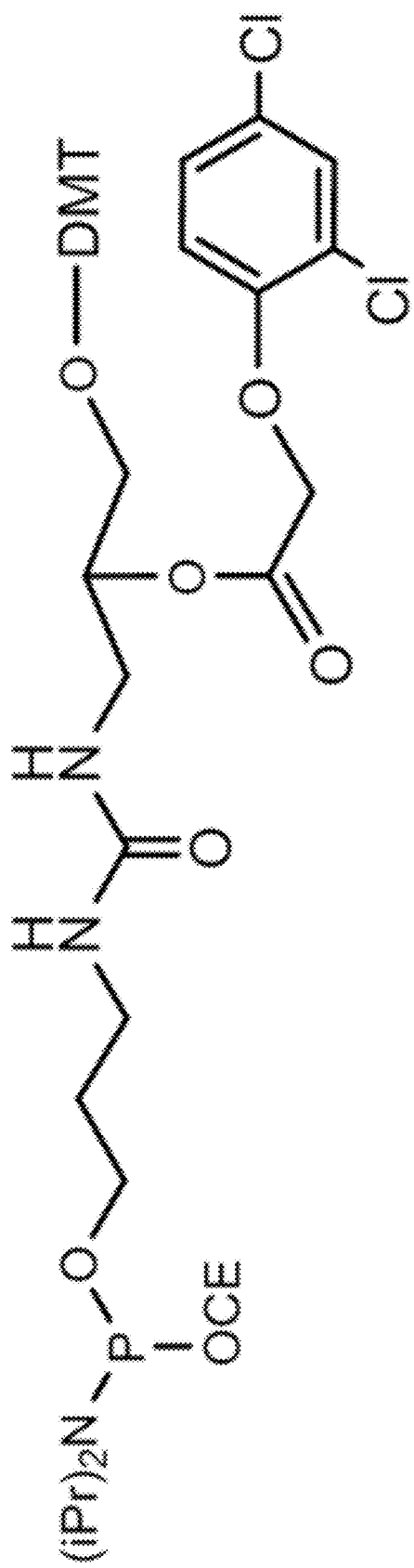
FIG. 3B shows an exemplary intermediates leading to cleavable linker (CL).
Figure 3C:
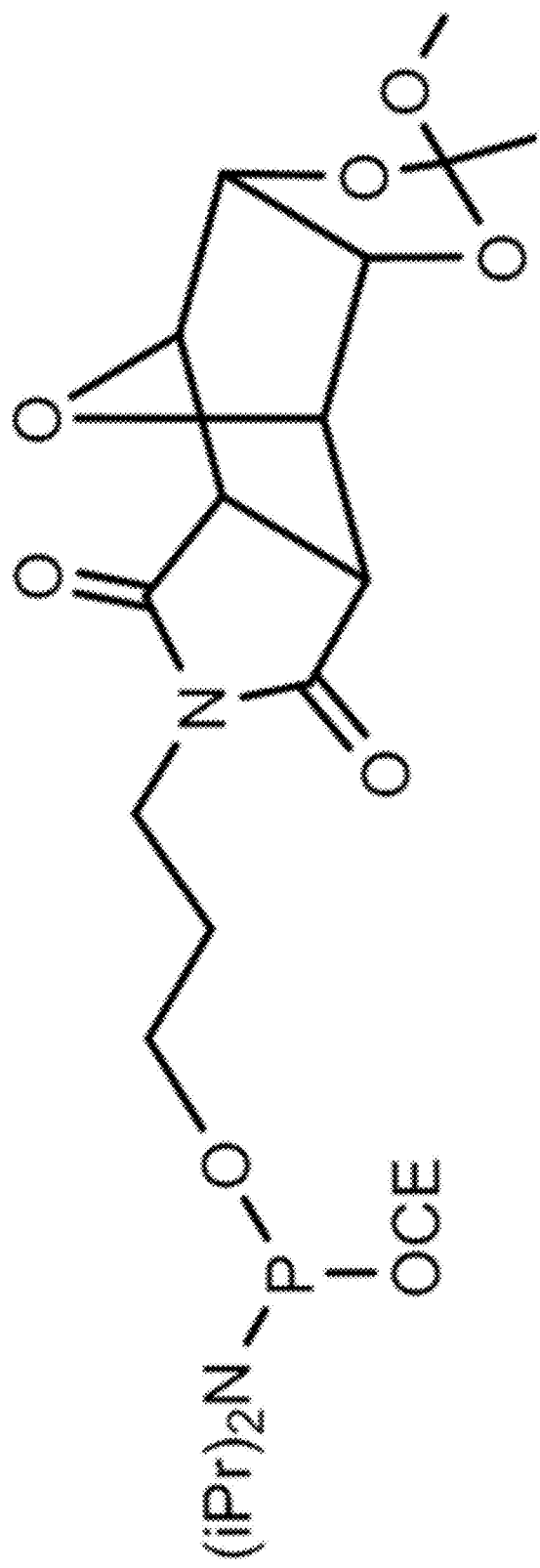
FIG. 3C shows an exemplary intermediates leading to cleavable linker (CL).

Specifically, after a free hydroxyl group is formed, a cleavable linker amidite intermediate (CL) can be incorporated into the branched linker, such as the cleavable linkers shown in FIG. 1B (middle panel), FIG. 3A, FIG. 3B, and FIG. 3C. Cleavable linkers can be added to the synthesis substrate using standard DNA synthesis protocols. In some cases, cleavable linkers can be added to the synthesis substrate using standard DNA synthesis protocols with extended coupling times (e.g., 3 minutes).

Standard oligonucleotide probe synthesis can then be conducted on the cleavable linker via its free hydroxyl group to synthesize probe sequences. The synthesized probe sequences can comprise full-length probe sequences and truncated probe sequences. Full-length probe sequences can comprise a linker group on the 5' end with a bromo (e.g., bromine) group (see, e.g., FIG. 1A) or an iodide group or other leaving groups at one end. For example, the last coupling of a DNA synthesis protocol can be performed with 5'-bromohexyl phosphoramidite to provide a bromine group at the 5' end of the synthesized oligonucleotides. In some cases, full-length probe sequences can comprise an —OH group on the 5' end, and the —OH group can react with reagents to add a linker with desired leaving group (such as Br, I, tosylate, mesylate, and triflate) on its end. These leaving groups, on the 5' ends of full-length probe sequences, can then be converted to other groups, such as azide groups. For example, a solution of sodium azide and sodium iodide in DNIF can be used to react synthesized oligonucleotides with a leaving group on its 5' end to provide azide groups. In some cases, the synthesis substrate can be washed (e.g., with acetonitrile) before and/or after reaction with azide groups.

In one example, controlled pore glass (CPG) beads are used as the synthesis substrate, and oligonucleotide probes are synthesized on cleavable linkers attached to the substrate. The beads are washed in a column with acetonitrile and dried under nitrogen gas. The washed beads are then added to a solution of 13 milligrams (mg) sodium azide and 30 mg sodium iodide in 2 milliliters (mL) of dry DNIF and allowed to react for 1 hour at 65° C. The reaction mixture is then cooled and solvent is removed with a pipette, and the beads are washed twice with 2 mL of DNIF and 2 mL of acetonitrile. Then, the beads are transferred to a column and dried under nitrogen gas. The 5' terminal hydroxyl group of oligonucleotides can also be converted into azide-containing linker group following a reported protocol published by Eric T Kool (J Org Chem. 2004, 69, 2404-2410).

Azide groups on the ends of full-length probe sequences can be circularized to another branch of the same or different branched linker, for example, as shown in the third row in FIG. 1A. Circularization can be accomplished through click chemistry (e.g., Cu(I) click chemistry or Cu⁺ click chemistry). Catalyst for the click chemistry can be Cu(I) salts, or Cu(I) salts made in situ by reducing Cu(II) reagent to Cu(I) reagent with a reducing reagent (Pharm Res. 2008 October; 25(10): 2216-2230). Known Cu(II) reagents for the click chemistry are commercially available, including but not limited to Cu(II)-(TBTA) complex and Cu(II) (THPTA) complex. TBTA, which is tris-[(1-benzyl-1H-1,2,3-triazol-4-yl)methyl]amine, also known as tris-(benzyltriazolylmethyl)amine, is a stabilizing ligand for Cu(I) salts. THPTA, which is tris-(hydroxypropyltriazolylmethyl)amine, is another stabilizing agent for Cu(I). Circularization can also be accomplished using copper-free click DNA ligation, such as by the ring-strain promoted alkyne-azide cycloaddition reaction (see, e.g., Chem. Commun., 2011, 47:6257-6259 or Nature, 2015, 519(7544):486-90).

Circularization can be conducted such that only full-length probe sequences are circularized. The cleavable linker can then be cleaved, for example by standard deprotection with a base, including but not limited to, ammonia, methyl amine, 1,2-diaminoethane, and potassium carbonate. Cleavage of the cleavable linker can release the 3'-OH terminus of the probe sequences, releasing truncated probe sequences and inverting circularized full-length probe sequences as shown in the third row of FIG. 1A.

Due to the sizes of and steric constraints placed on the full-length probe sequences, the efficiency and the location of the click chemistry reaction between the alkyne and the azide can vary. In one embodiment, the circularization forms covalent bonds between an alkyne group and an azide group, both of which are attached to the same branched linker. In another embodiment, the circularization forms covalent bonds between an alkyne group and an azide group, each attached to a different branched linker. Although an intramolecular reaction (with respect to the same branched linker) is generally favored over an intermolecular reaction (between two different branched linkers), the reactivity of the precursors coupled with steric hindrance can make intermolecular reaction more favorable, especially when there are more candidates for intermolecular reaction than for intramolecular reaction or when the candidates for intermolecular reaction is more accessible than those for intramolecular reaction due to steric hindrance. The efficiency of circularization as used herein refers to the conversion rate of azide to 1,2,3-triazole on the substrate.

One way of influencing the efficiency of the click chemistry reaction is to change the ratio between the alkyne and the azide groups on the substrate. This can be achieved by reacting the available hydroxyl groups on the second linker with a mixture of an intermediate for the introduction of the cleavable linker intermediate and a capping moiety. Such capping moieties can be an acyl, dialkoxyphosphoryl, alkyl, alkoxycarbonyl, or dialkyaminocarbonyl group, which can react with free hydroxyl groups and make the hydroxyl group unavailable for the attachment of a cleavable linker and an ensuing azide-bearing oligonucleotide. The presence of the cap moiety on the branched linker, not only reduces the steric hindrance associated with oligonucleotides, but it also provides a higher alkyne to azide ratio to improve the efficiency of circularization based on the consumption of the azide group. The azide group can have multiple neighboring alkyne groups to react with when capping moiety is added together with the intermediate for the introduction of the cleavable linker.

Finally, the current disclosure allows the introduction of azide-bearing oligonucleotides and alkynes to the support via individual phosphoramidite monomers, which react with hydroxyl groups on the surface, instead of introducing both the oligonucleotides and alkyne on branched linkers.

Linkers used, including branched linkers and cleavable linkers, can be stable during oligonucleotide probe synthesis processes such as those discussed herein. Stability of linkers can allow oligonucleotide probe synthesis without the use of protection-deprotection steps to preserve the linkers. Linkers can lack reactive species. The absence of reactive species from the linkers can result in the linkers being inert during a DNA synthesis process, which can remove the need for protection-deprotection steps. In some cases, at least about 10%, 20%, 30%, 40%, 50%, 60%, 70%, 75%, 80%, 85%, 90%, 95%, 96%, 97%, 98%, 99%, 99.9%, 99.99%, or 99.999% of linkers present prior to DNA synthesis remain intact after DNA synthesis.

The probe inversion techniques discussed herein can be conducted in aqueous media. Avoidance of the use of organic solvents can make such techniques more environmentally friendly and increase the ease of chemical handling and waste disposal.

The probe inversion techniques discussed herein can be conducted at a pH of at least about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, or 13.5. The probe inversion techniques discussed herein can be conducted at a pH of at most about 14.0, 13.5, 13.0, 12.5, 12.0, 11.5, 11.0, 10.5, 10.0, 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, or 0.5. The probe inversion techniques discussed herein can be conducted at a pH of about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, or 13.5. In some cases, the probe inversion techniques discussed herein can be conducted at or about physiological pH, such as about 7.365 or about 7.5. Conducting reactions at physiological pH can reduce or obviate the need for handling harsh substances or reaction conditions, and can employ aqueous media.

The probe inversion techniques discussed herein can be conducted at a temperature of about 15° C., 20° C., 25° C., 30° C., or 35° C. The probe inversion techniques discussed herein can be conducted at a temperature of at most about 15° C., 20° C., 25° C., 30° C., or 35° C. The probe inversion techniques discussed herein can be conducted at a temperature of at least about 15° C., 20° C., 25° C., 30° C., or 35° C. In some cases, the probe inversion techniques discussed herein can be conducted at or about room temperature, such as about 20° C., about 21° C., about 22° C., about 23° C., about 24° C., about 25° C., about 26° C., from about 20° C. to about 26° C., or from about 20° C. to about 22° C. Conducting reactions at room temperature can reduce or obviate the need for handling harsh substances or reaction conditions.

Releasing truncated probe sequences can increase the percentage of full-length sequences present in the array. In some cases, at least about 10%, 20%, 30%, 40%, 50%, 60%, 70%, 80%, 90%, 95%, 96%, 97%, 98%, 99%, 99.9%, 99.99%, or 99.999% of probes remaining bound to the array substrate following a probe inversion process are full-length sequences. In some cases, a probe inversion process can release at least about 10%, 20%, 30%, 40%, 50%, 60%, 70%, 80%, 90%, 95%, 96%, 97%, 98%, 99%, 99.9%, 99.99%, or 99.999% of truncated probes bound to the array substrate prior to the probe inversion process.

The synthesis substrate can comprise different forms or shapes, such as a bead or a flat array. The synthesis substrate can comprise any suitable material, including but not limited to glass (e.g., controlled pore glass), silicon, or plastic. Substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

Inverted probes can provide many advantages over standard non-inverted probes, for a variety of applications. For example, as discussed above, probe inversion can remove most or all unwanted truncated sequences, thereby providing a population of inverted probes containing up to 100% full length sequences. Additionally, inverted probes can have the 3' OH group free, which can be beneficial for conducting enzymatic reactions (e.g., single or multiple base extension, ligase reaction). The inverted probes can also be used for sequencing by synthesis (SBS).

EXAMPLES

Example 1—Probe Inversion on Controlled Pore Glass

Figure 1C:
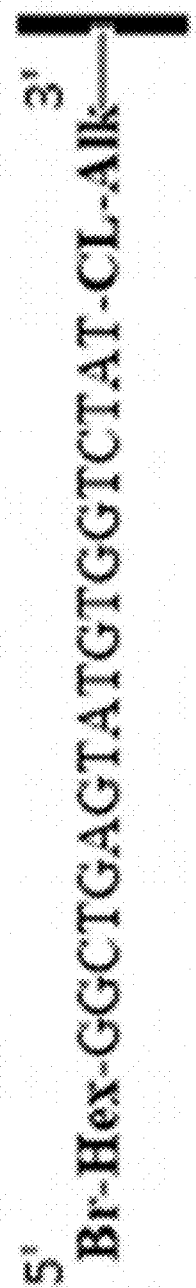
FIG. 1C shows an exemplary oligonucleotide (SEQ ID NO: 1) used for probe inversion incorporating intermediates in FIG. 1B.

Branched linker phosphoramidites having an alkyne moiety were coupled to a dT-derivatized controlled pore glass (CPG) solid support on a DNA synthesizer using standard DNA synthesis protocols (see, e.g., FIG. 1A). Then, cleavable linkers (CL, see FIG. 1B) were attached to the branched linkers (Alk, see FIG. 1B) using standard procedures, followed by synthesis of 19-mer DNA sequences (5'-GGCTGAGTATGTGGTCTAT-3' (SEQ ID NO: 1)). In the last oligonucleotide coupling step, 5'-bromohexyl phosphoramidite (Br-Hex, see FIG. 1B) was incorporated (see FIG. 1C). DNA synthesis was conducted using an ABI 394 DNA synthesizer using standard DNA synthesis protocols. Extended coupling time (3 minutes) was used for all linker phosphoramidites (Alk, CL, and Br-Hex).

Once DNA synthesis was complete, the 5'-bromo groups were transformed into azide groups by treating the oligonucleotides on the CPG solid support with $NaN_3$/NaI in DMF at 65° C. for 1 hour. 13 mg of sodium azide ($NaN_3$) and 30 mg of sodium iodide (NaI) were dissolved in 2 mL of dry DNIF; this solution was then added to the oligonucleotides loaded on CPG beads in a 2 mL Eppendorf. The reaction mixture was heated at 65° C. for 1 hour. After cooling down, the reaction mixture and CPG beads were transferred back to a column. The beads were washed with water (4 mL) and acetonitrile (6 mL), and then dried under nitrogen.

Click circularization was then performed using copper catalyzed azide-alkyne cycloaddition (CuAAC) chemistry. An ascorbic acid stock solution was prepared fresh at a concentration of 5 mM (e.g., 1.8 mg ascorbic acid in 2.0 mL water). A copper (II)-TBTA stock solution was prepared at a concentration of 10 mM copper (II)-TBTA in 55% DMSO (e.g., a solution of 5 mg $CuSO_4$ in 1 mL water mixed with a solution of 11.6 mg TBTA in 1.1 mL DMSO are mixed). CPG beads with alkyne-azide modified oligonucleotides were mixed with 55 μL of water in a pressure-tight vial. 20 μL of 2 M triethylammonium acetate (TEAA) buffer (pH 7.0) was added to the vial, followed by addition of 95 μL of DMSO. The vial was vortexed. Then, 20 μL of 5 mM ascorbic acid stock solution was added to the vial, and briefly vortexed. The solution was degassed by bubbling nitrogen into it for 1 minute. 10 μL of the 10 mM copper (II)-TBTA stock solution was added to the vial. The vial was then flushed with nitrogen gas, sealed, vortexed thoroughly, and incubated overnight at room temperature. The final concentrations in the vial were about 0.5 μmol CPG beads, about 50 vol % DMSO, about 50 vol % water, 0.5 mM ascorbic acid, 0.2 M TEAA buffer, and 0.5 mM Cu-TBTA complex.

Only full length oligonucleotides possessing azide functionality were circularized (see, e.g., FIG. 1A). Once click circularization was accomplished, the oligonucleotides were de-protected and cleaved from the cleavable linker (CL) sites using standard de-protection conditions (e.g., treatment with $NH_4OH$ at 55° C. for 15 hours).

Figure 4A:
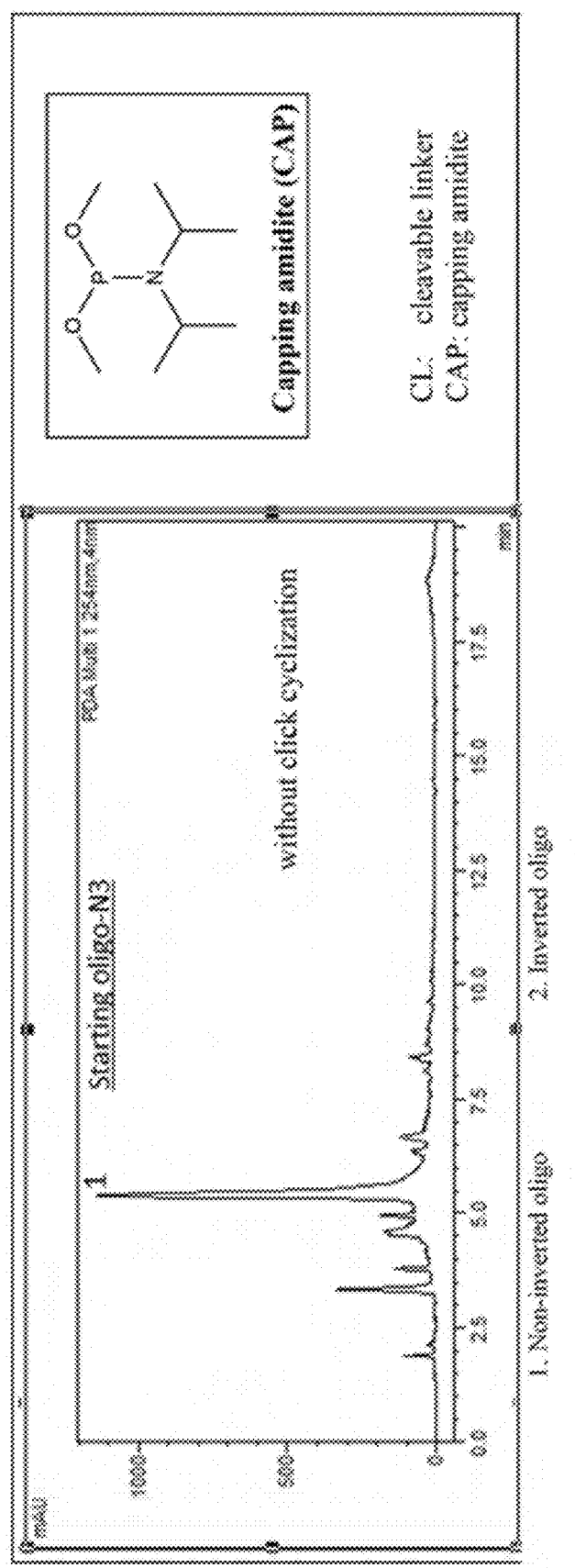
FIG. 4A shows an exemplary HPLC profile of non-inverted oligonucleotides.
Figure 4B:
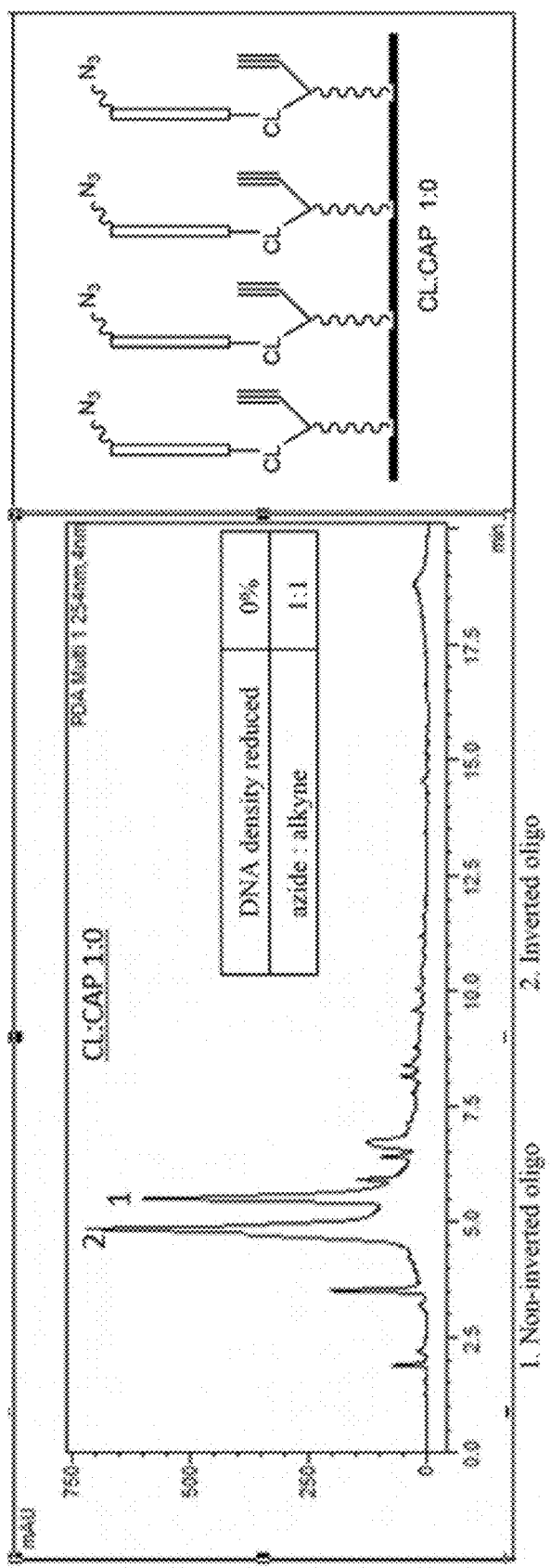
FIG. 4B shows an exemplary HPLC profile of inverted oligonucleotides without capping phosphoramidites.

The click circularization and probe inversion efficiency were tested by comparing the HPLC profile of standard non-inverted oligonucleotides (see FIG. 4A) with the HPLC profile of inverted oligonucleotides (FIG. 4B). Peaks labeled "1" correspond to non-inverted oligonucleotides, while peaks labeled "2" correspond to inverted oligonucleotides. HPLC analysis showed that about 70% of oligonucleotides were inverted under the tested reaction conditions. Increasing the click circularization reaction time from overnight to 3 days did not increase percentage of inverted oligonucleotides.

Figure 4C:
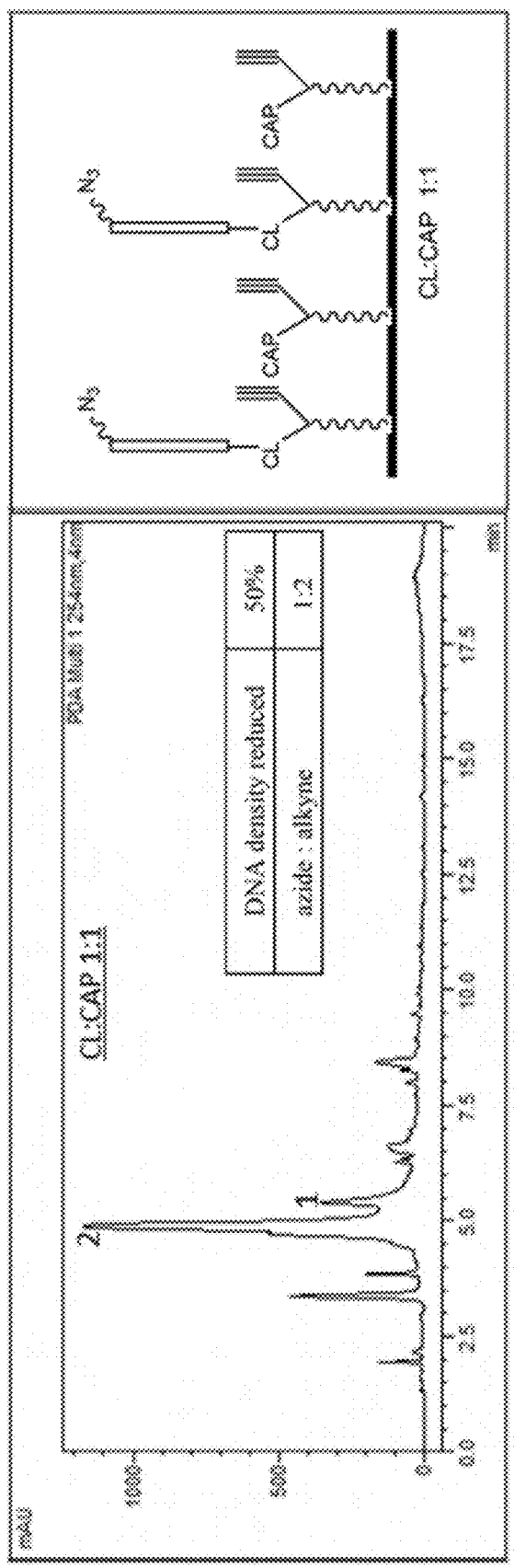
FIG. 4C shows an exemplary HPLC profile of inverted oligonucleotides with a 1:1 ratio of cleavable linkers to capping phosporamidites.
Figure 4D:
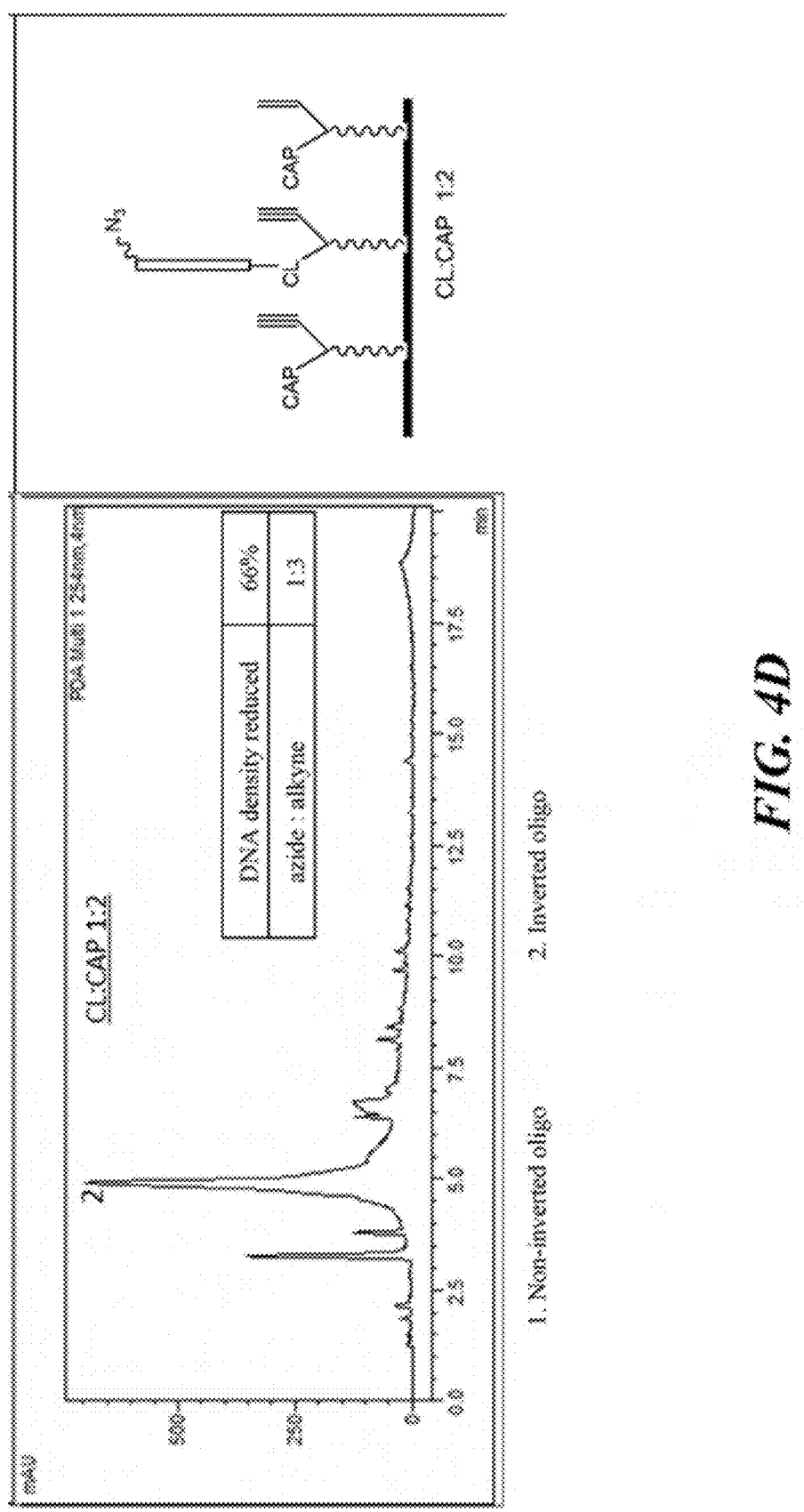
FIG. 4D shows an exemplary HPLC profile of inverted oligonucleotides with a 1:2 ratio of cleavable linkers to capping phosporamidites.
Figure 5A:
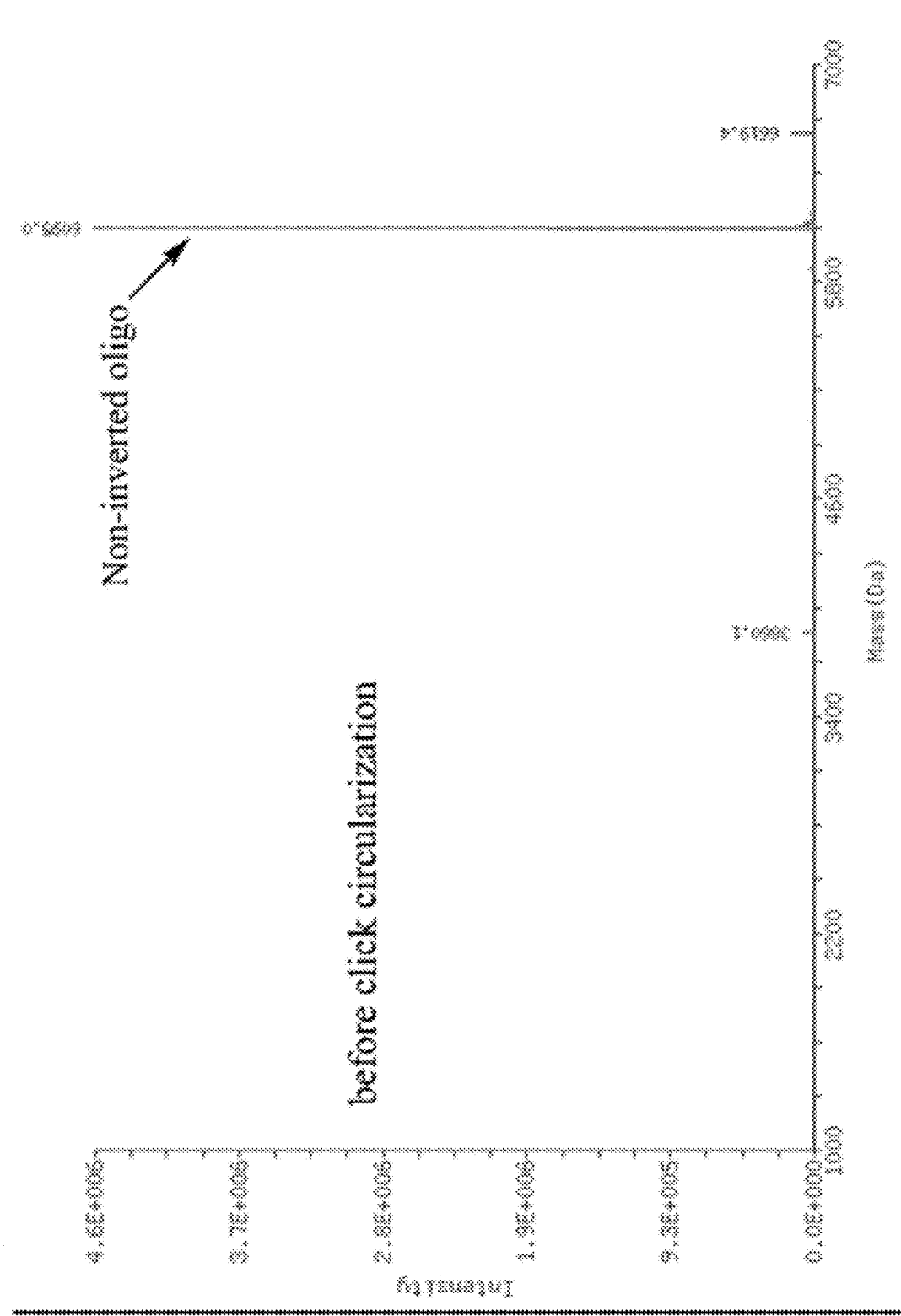
FIG. 5A shows an exemplary mass spectrograph of non-inverted oligonucleotides.
Figure 5B:
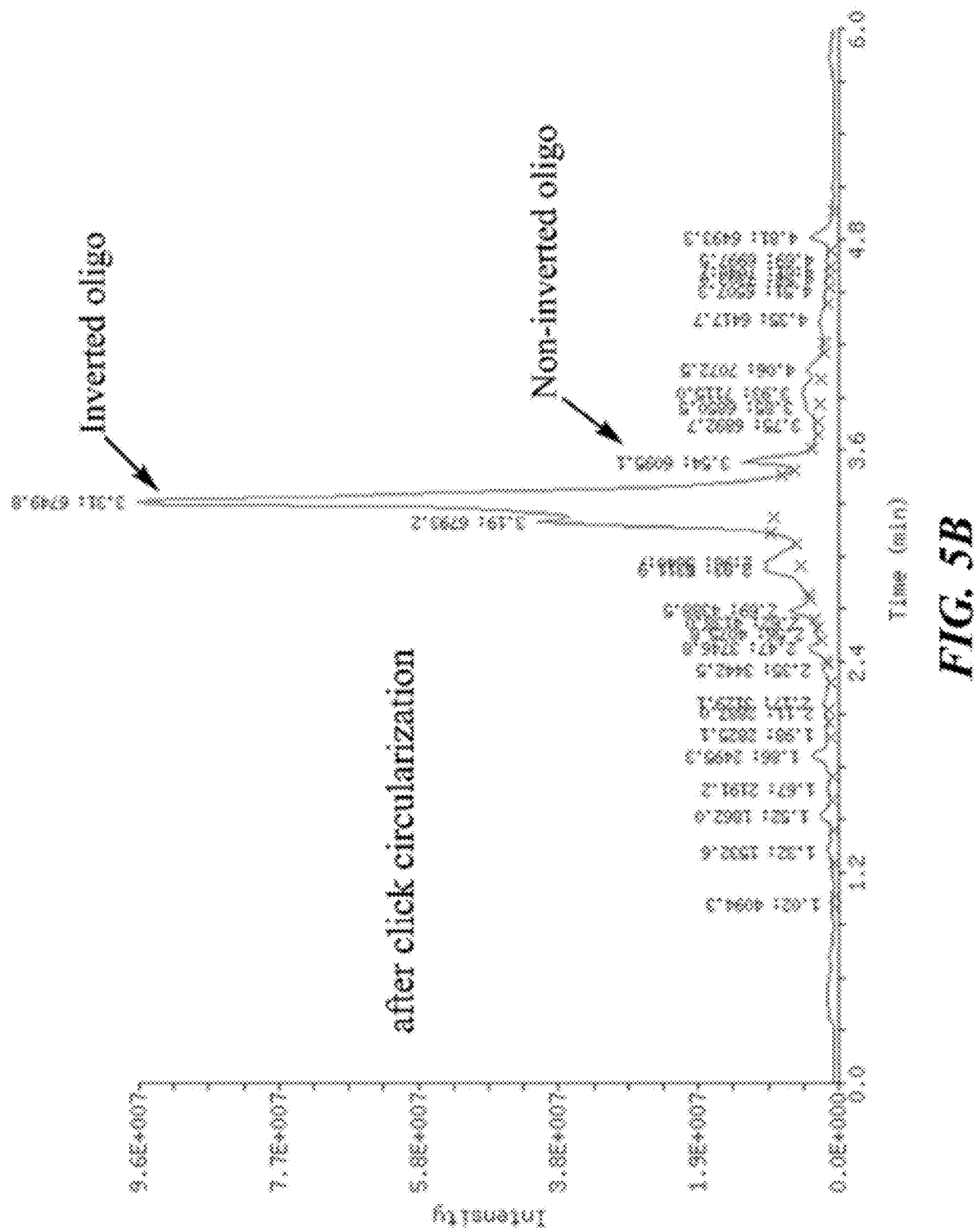
FIG. 5B shows an exemplary mass spectrograph of inverted oligonucleotides.

Reduced efficiency of click circularization may be attributed to steric hindrance of DNA molecules on dense CPG solid supports. In order to reduce DNA probe density on the solid support, a mixture of cleavable linkers (CL) and capping phosphoramidites (CAP, see the insert in FIG. 4A) was used in different ratios (e.g., 1:0, 1:1, 1:2) immediately after the first phosphoramidite (branched linker, Alk) coupling. Using a capping phosphoramidite (CAP) directly after a branched linker (Alk) coupling step can reduce the oligonucleotide density on the solid support, and can increase the percentage of alkyne which can eventually helped in click circularization (see FIGS. 4A-4D, right panels). A 50% reduction in DNA density (CL:CAP 1:1; azide:alkyne ratio 1:2, FIG. 4C) resulted in inversion of approximately 90% of oligonucleotides. A 66% reduction in DNA density (CL:CAP 1:2; azide:alkyne ratio 1:3, FIG. 4D) afforded about 100% inversion of the oligonucleotides. The existence of inverted oligonucleotides was reaffirmed by comparing the mass spectra of non-inverted (see FIG. 5A) before click circularization to that of inverted oligonucleotides (see FIG. 5B) after click circularization.

Example 2—Probe Inversion on Chip

DNA synthesis on chips (e.g., silanated glass surfaces) was conducted similarly to the protocols described in G. H. McGall, F. A. Fidanza, Photolithographic synthesis of arrays. In *Methods in Molecular Biology: DNA Arrays, methods and Protocols*; J. B. Rampal, Ed.; Humana Press: Torowa, N.J., 2001; Vol. 170, 71-101. DNA density reduction was not deemed necessary for on-chip oligonucleotide inversion, as inversion efficiency was similar with and without density reduction. In order to make specific DNA features on the chips, photo-cleavable phosphoramidites were used instead of standard DMT-phosphoramidites.

After DNA synthesis, the 5'-bromo groups were converted into azides by treatment with a mixture of $NaN_3$ and NaI in DMF at 65° C. for 2 hours. 13 mg of sodium azide (NaN3) and 30 mg of sodium iodide (NaI) were dissolved in 2 mL of dry DMF; the solution was then added via syringe to a flow cell containing the chip, and the reaction mixture was heated at 65° C. for 2 hours, with fresh reaction mixture pushed into the flow cell after 1 hour. After cooling down to room temperature, the reaction mixture was removed and the oligonucleotides were washed with DMF, water, and acetonitrile, and dried under nitrogen.

Full length oligonucleotides were then circularized using CuAAC click chemistry (see, e.g., FIG. 1A). The flow cell containing the chip was flushed with nitrogen gas for about 5-10 minutes. A reaction mixture was prepared as follows: 275 µL of water was added to a 2 mL Eppendorf tube, followed by 100 µL of 0.2 M triethylammonium acetate (TEAA buffer) at pH 7.0 and 475 µL of DMSO. The mixture was vortexed, 100 µL of 5 mM ascorbic acid stock solution (as described in Example 1) was added, and the mixture was briefly vortexed. The solution was then degassed by bubbling with nitrogen gas for 2 minutes. 50 µL of 10 mM copper (II)-TBTA stock solution (as described in Example 1) was added to the mixture. The mixture was flushed with nitrogen gas for 1 minute, then added via syringe to the chip under a nitrogen atmosphere. The click circularization reaction was carried out at room temperature for 24 hours.

After click circularization, oligonucleotides were de-protected with a 50% $EDA/H_2O$ mixture. EDA treatment was used to de-protect DNA bases and to cleave the 3' end of the oligonucleotides from the cleavable linker (CL) sites. The chip was incubated in a 1:1 mixture of ethylene diamine (EDA) and water at room temperature for 7 hours, with the $EDA:H_2O$ de-protection mixture exchanged with freshly prepared $EDA:H_2O$ mixture every 2 hours. Thereafter chips were washed thoroughly with water and then stored at 4° C. This step removed truncated as well as non-circularized oligonucleotides, allowing only full-length inverted oligonucleotide sequences to remain attached to the solid surface. The EDA treatment also made the 3'-OH group available for further enzymatic interventions (see, e.g., FIG. 1A).

Figure 6A:
FIG. 6A shows an exemplary fluorescence image of a control chip with no oligonucleotides.
Figure 6B:
FIG. 6B shows an exemplary fluorescence image of a control chip with non-inverted oligonucleotides.
Figure 6C:
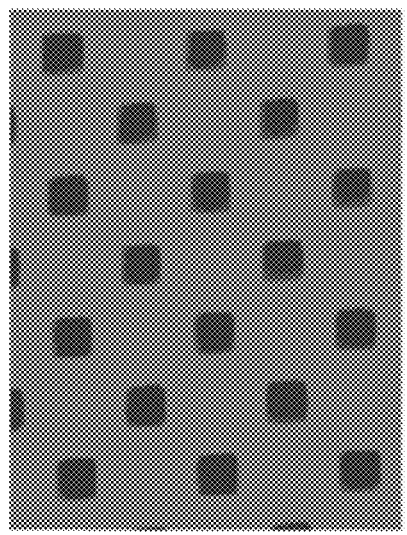
FIG. 6C shows an exemplary fluorescence image of a chip with inverted oligonucleotides.

To visualize on-chip inverted oligonucleotides, Cy3-labeled DNA sequences, complementary to the inverted sequences, were used for hybridization (see, e.g., FIGS. 6A-6C). Inverted oligonucleotides were hybridized with Cy3 labelled complementary DNA sequences by placing a 500 nM DNA solution in 4x saline sodium citrate buffer (SSC) on the top of the chip. The reaction mixture was incubated at 45° C. for 1 hour. Thereafter chip was washed several times with 4xSSC buffer. The presence of fluorescent signals from the Cy3 probes after hybridization confirmed the presence of the inverted oligonucleotides on the chip (see FIG. 6C). However, no fluorescent signals were observed either from a control chip having no oligonucleotides (FIG. 6A) or from a chip where oligonucleotides were de-protected and cleaved without click circularization (FIG. 6B). These experiments confirmed that all the on-chip oligonucleotides were inverted.

The presence of 3'-OH groups on the inverted oligonucleotides was confirmed and visualized by primer extension using fluorescent dNTPs (see, e.g., FIG. 7). The inverted oligonucleotides were first hybridized with DNA templates (5'-CGAACGACGCAATAGACCACATACTCAGCC-3' (SEQ ID NO: 2)) by incubating the chip with 1 µM of DNA template in 4xSSC at 45° C. for 1 hour. Thereafter, excess DNA template was washed away from the chip with water. An extension reaction mixture was prepared with 5 µL of 10x standard Taq buffer (final amount: 1x), 8 µL of 5 units/µL TaqDNA polymerase solution (final amount: 40 units), 10 µL of 10 µM dNTPs comprising Alexa568-dUTP, dATP, dCTP, and dGTP (final concentration 2 µM), and 27 µL of water. The extension reaction mixture was placed on top of the chip with hybridized DNA template and incubated at 50° C. for 2 hours in a sealed box under a humid atmosphere. Following extension, the chip was washed with water prior to imaging.

Figure 7B:
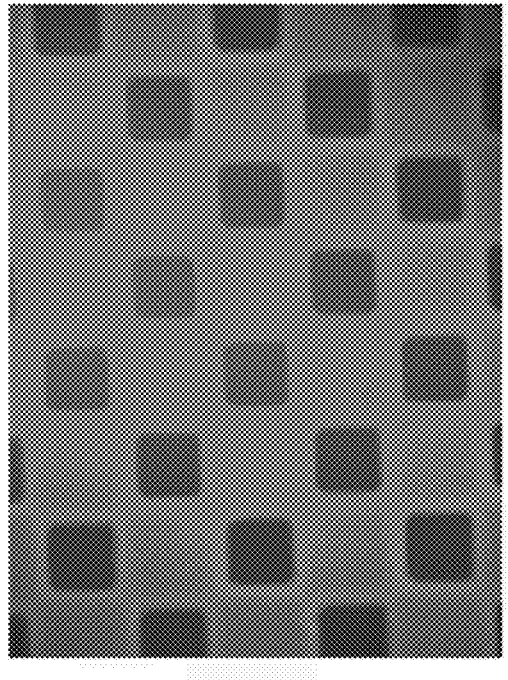
FIG. 7B shows an exemplary fluorescence image of a chip with inverted extended oligonucleotides.
Figure 7D:
FIG. 7D shows an exemplary fluorescence image of a chip with non-inverted oligonucleotides after an extension reaction.
Figure 7A:
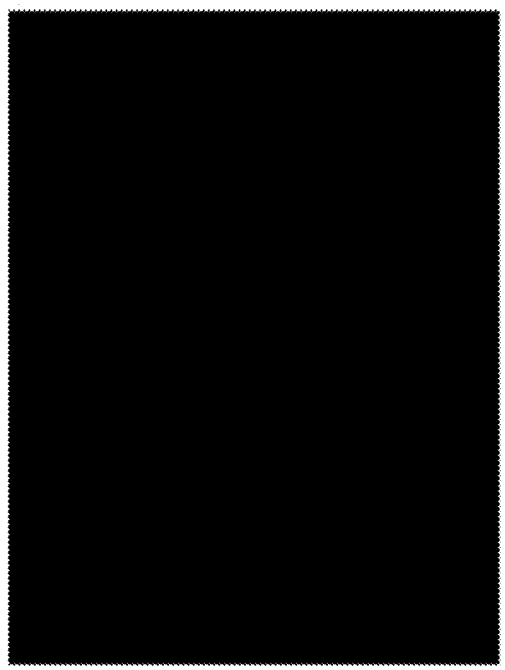
FIG. 7A shows an exemplary fluorescence image of a chip with inverted oligonucleotides prior to an extension reaction.
Figure 7C:
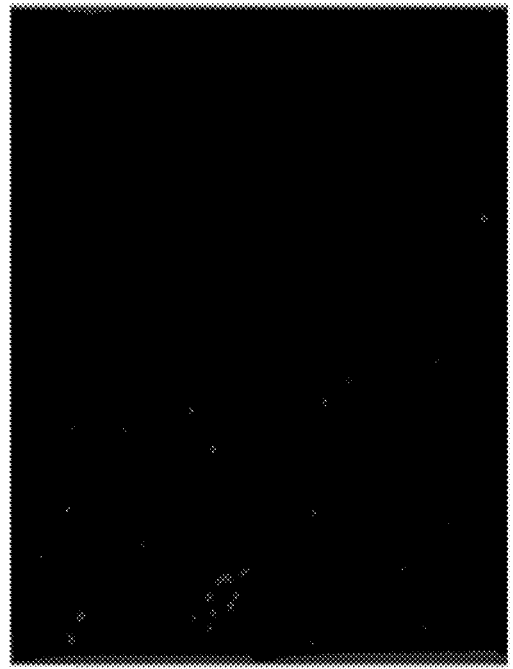
FIG. 7C shows an exemplary fluorescence image of a chip with non-inverted oligonucleotides prior to an extension reaction.

Fluorescent scanning showed strong signals from the extended part of inverted oligonucleotides (FIG. 7B), while no fluorescence was noted in the control chip containing no oligonucleotides (FIG. 7A). To control for the possibility of nonspecific primer extension at 5'OH terminals, primer extension was performed on standard non-inverted oligonucleotides having free 5'OH. In this case too, no fluorescent signals were observed before (FIG. 7C) or after (FIG. 7D) conducting a primer extension reaction, indicating a lack of primer extension at the 5'OH terminal.

Example 3—Probe Inversion of ABI Synthesized Oligonucleotide Arrays

Figures 8A, 8B:
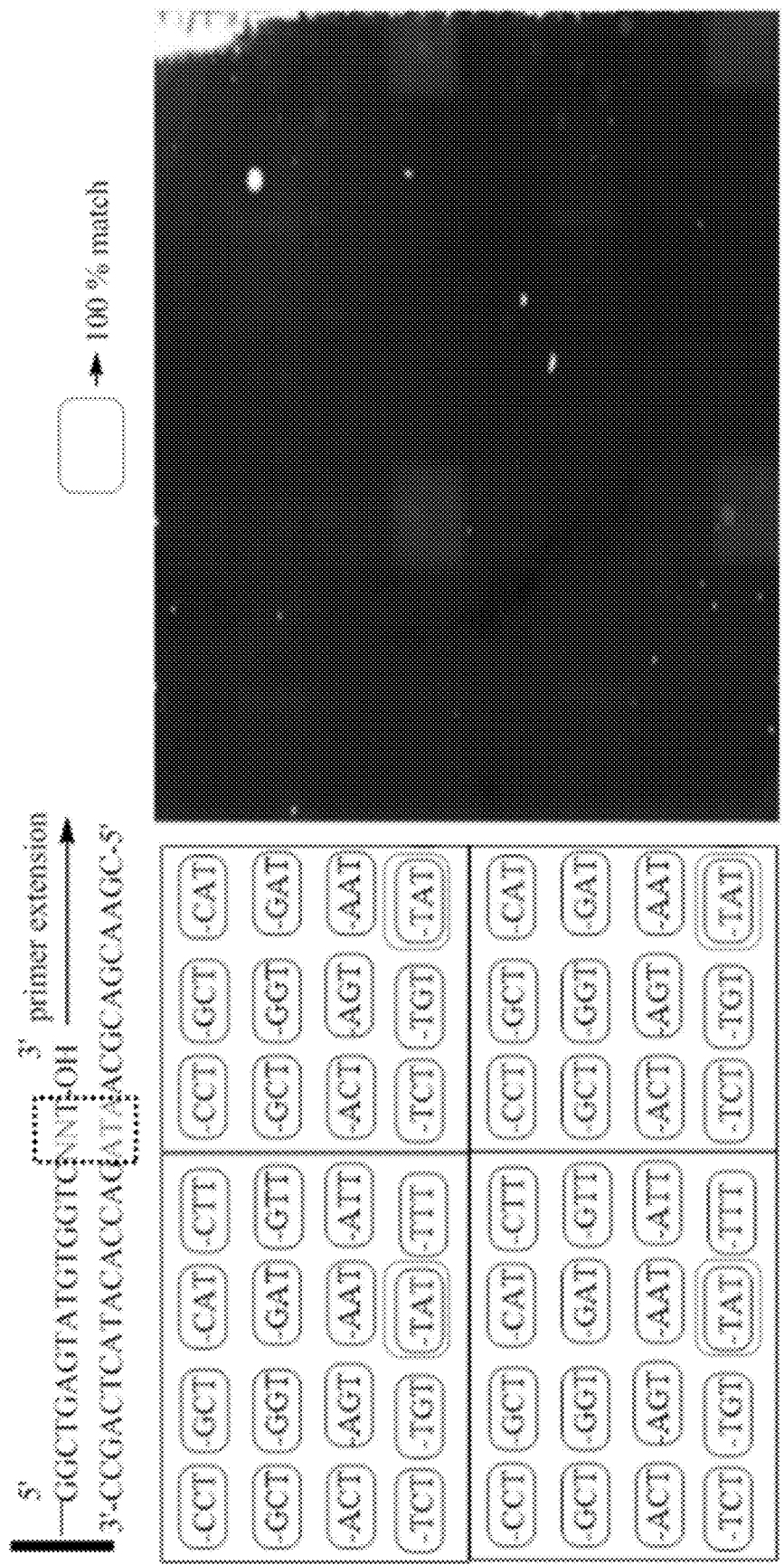
FIG. 8A shows a schematic of an array of oligonucleotides with different sequence permutations of -NNT-3' (SEQ ID NOS 4 and 5, respectively, in order of appearance).
FIG. 8B shows an exemplary fluorescence image of a chip with inverted oligonucleotides after an extension reaction.

Oligonucleotide arrays were synthesized on an ABI synthesizer and were inverted using copper-catalyzed azide alkyne cycloaddition reactions as discussed herein. One set of arrays was fabricated with the three nucleotides at the 3' end having the sequence -NNT-3' in its different permutations (e.g., -CCT-3', -GCT-3', -ACT-3', -TCT-3', etc., as shown in FIG. 8A). Another set of arrays was fabricated with the two nucleotides at the 3' end having the sequence -NN-3' in its different permutations (e.g., -CT-3', -GT-3', -AT-3', -TT-3', etc., as shown in FIG. 9A).

Next, the inverted oligonucleotides on the arrays were first hybridized with a DNA template complementary to those oligonucleotides ending with -TAT-3' or -AT-3'. Inverted oligonucleotides were hybridized with DNA by incubating the arrays with 1 mL of 1 μM DNA template in 4×SSC at 45° C. for 1 hour. Thereafter excess DNA template was washed away from the array first with 4×SSC and then with primer extension buffer.

Primer extension was then carried out with this template using Taq DNA polymerase. The extension reaction mixture contained Taq polymerase (8 uL, 40 units) and 1 μM of dNTPs (including Alexa568-dUTP) and was placed on top of the arrays with hybridized DNA template. The arrays were incubated at 50° C. for 1 hour in a sealed box under humid atmosphere. Once extension was complete, the arrays were washed with water prior to imaging.

Figures 9A, 9B:
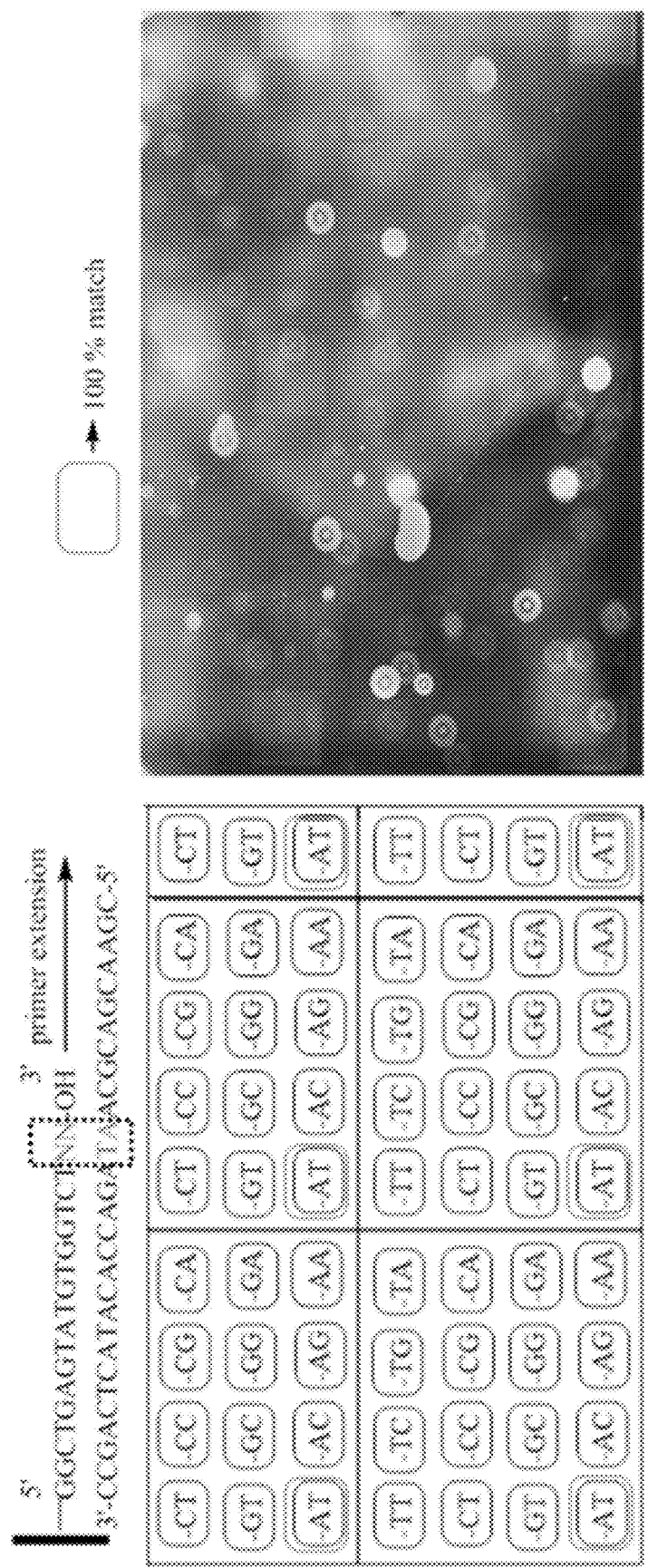
FIG. 9A shows a schematic of an array of oligonucleotides with different sequence permutations of -NN-3' (SEQ ID NOS 6 and 5, respectively, in order of appearance).
FIG. 9B shows an exemplary fluorescence image of a chip with inverted oligonucleotides after an extension reaction.

Imaging experiments showed signal the regions of the arrays where the 3' end of inverted oligonucleotides perfectly matched the template DNA (see FIG. 8B and FIG. 9B).

Example 4—On-Wafer Probe Inversion

Oligonucleotide arrays were synthesized on-wafer and were inverted using copper-catalyzed azide alkyne cycloaddition reactions as discussed herein.

Figure 10:
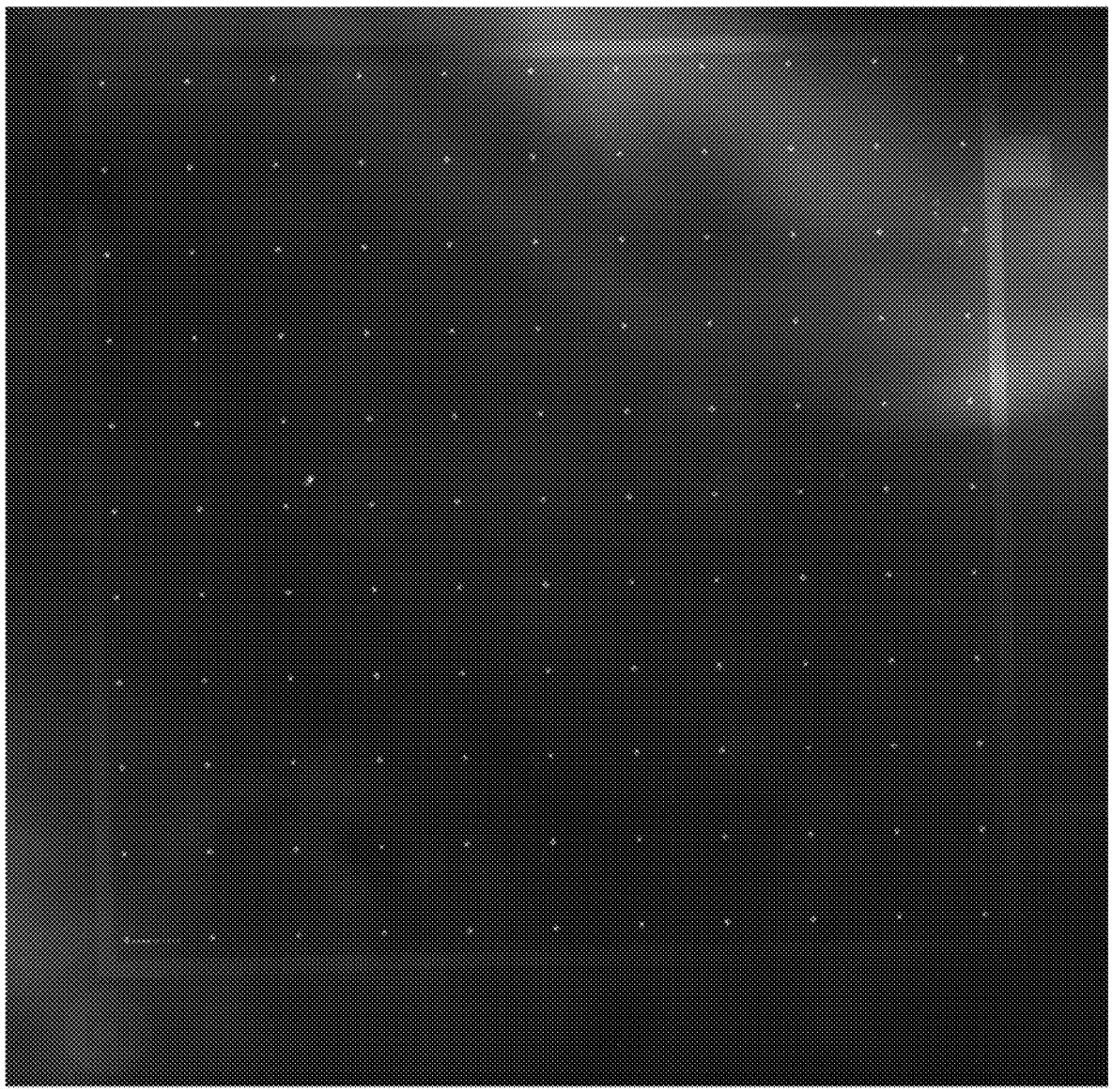
FIG. 10 shows an image of alignment marks on a wafer with inverted nucleotides hybridized with Cy3-labeled complementary DNA.

Next, the inverted oligonucleotide arrays on the wafer were analyzed by hybridizing alignment marks with a 400 μL of 1 μM Cy3-labeled complementary DNA sequence in 4×SSC buffer at 55° C. for 1 hour. Thereafter, any excess Cy3-labeled DNA was washed away from the array with 4×SSC prior to imaging. FIG. 10 shows an image of alignment marks on a wafer with inverted nucleotides hybridized with Cy3-labeled complementary DNA.

Single base primer extension (on the target sequence complementary to the on-chip inverted DNA sequence) was then carried out by hybridizing the top adapter (FC2') of the wafer chip with FC2 primer (complementary sequence to FC2') by incubating at 55° C. for 1 hour. The top adapter comprises a region at the top of the inverted sequences. Excess primer was washed away with 4×SSC, followed by a final wash with incorporation buffer.

Figure 11A:
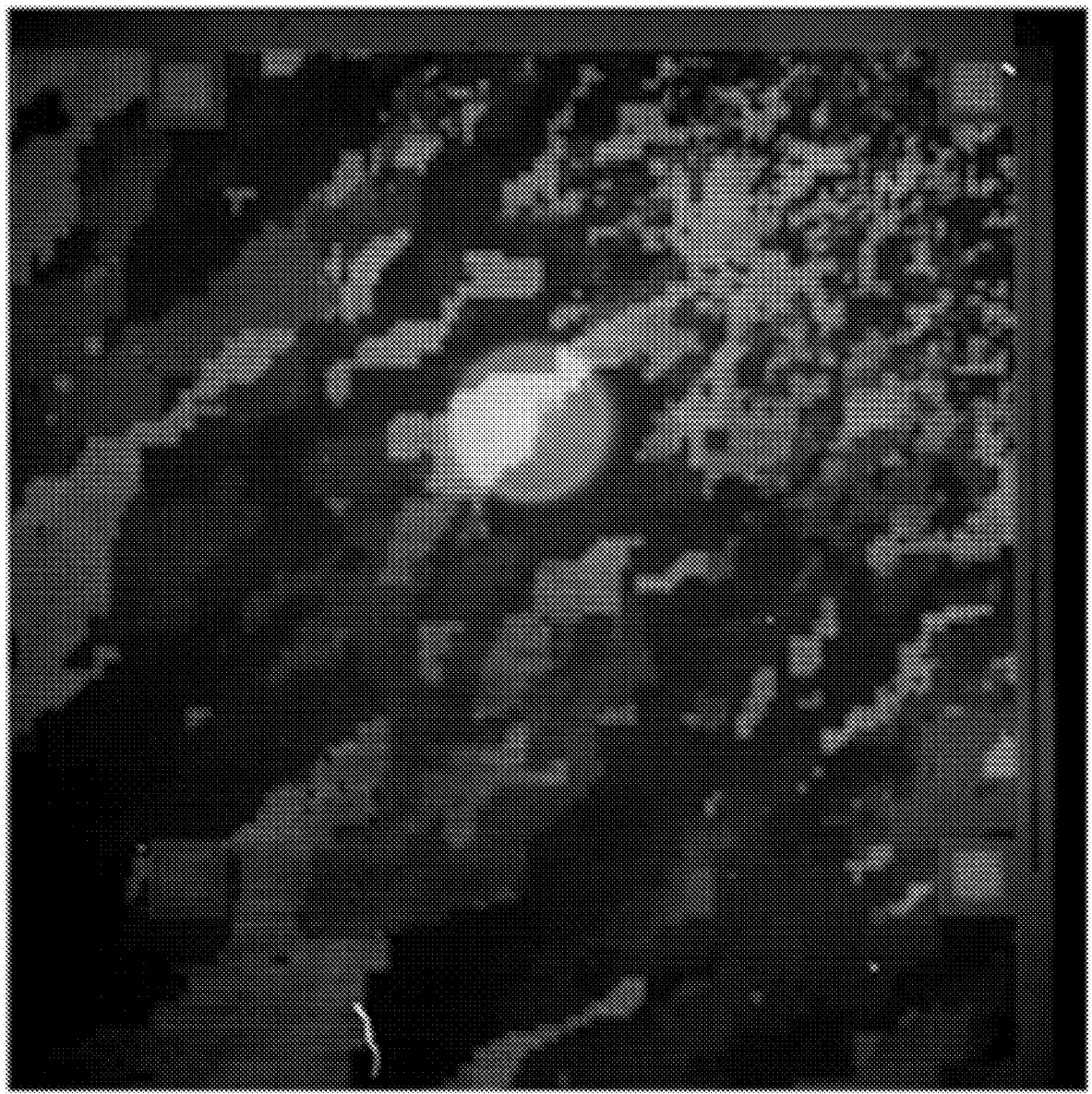
FIG. 11A shows an image of incorporation of dGTP nucleotides in a single-base extension.
Figure 11B:
FIG. 11B shows an image of incorporation of dTTP nucleotides in a single-base extension.
Figure 11C:
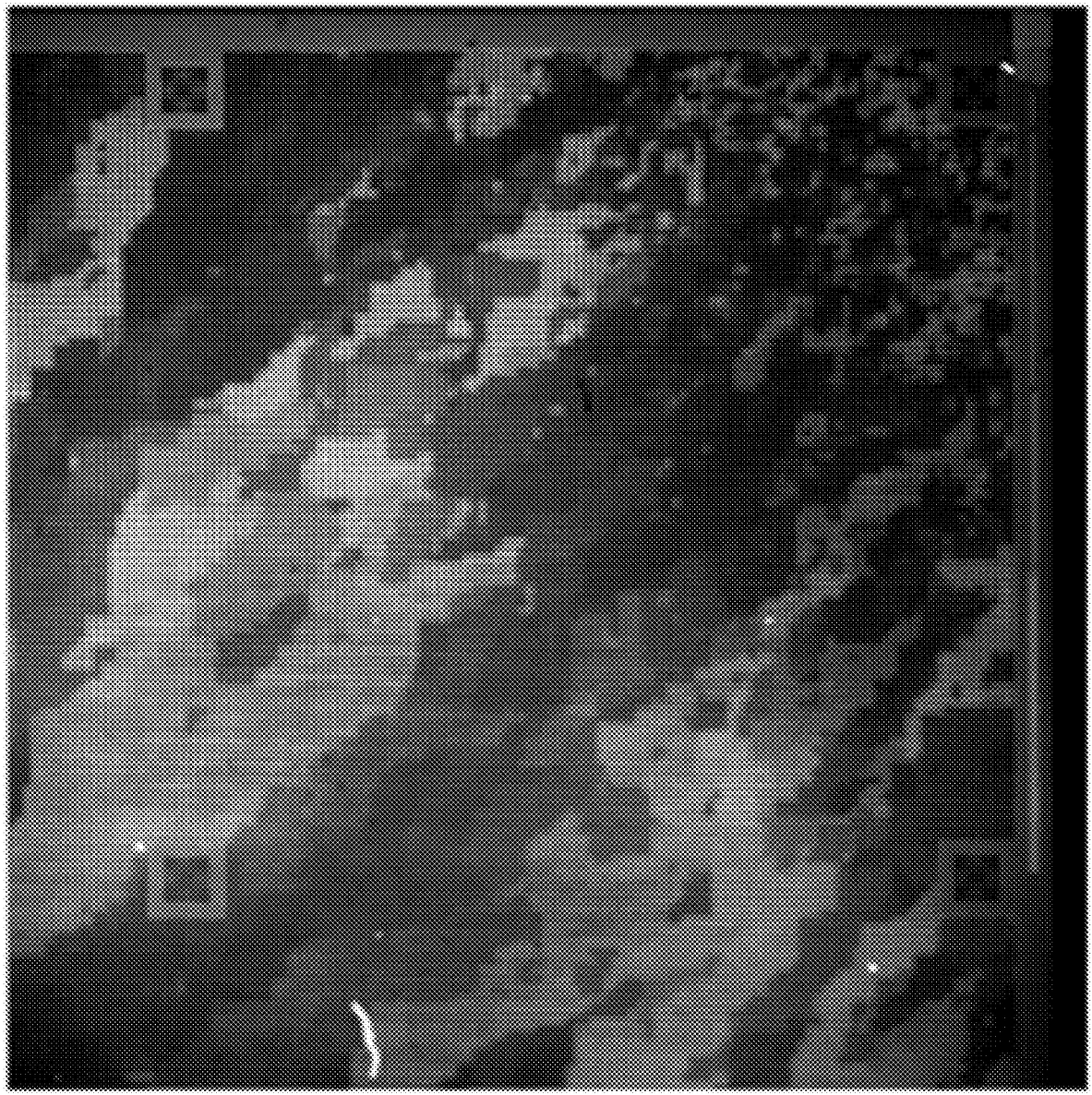
FIG. 11C shows an image of incorporation of dATP nucleotides in a single-base extension.
Figure 11D:
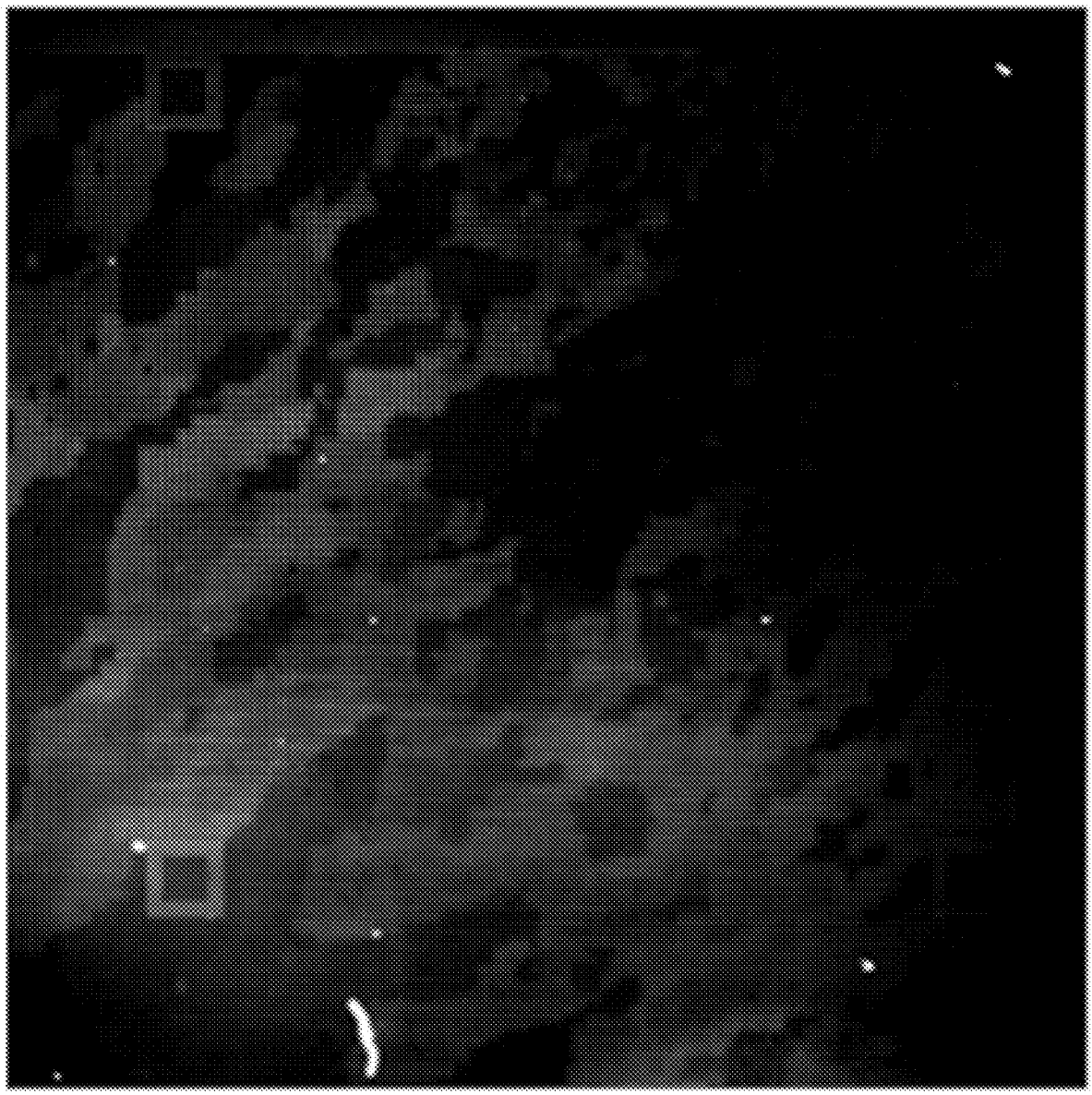
FIG. 11D shows an image of incorporation of dCTP nucleotides in a single-base extension.

Illumina incorporation reaction mixture (400 μL), containing DNA polymerase and fluorophore labelled reversible terminator dNTPs (all four nucleotides were labeled), was placed on top of the wafer chip which was already hybridized with FC2 primer. The chip was incubated at 50° C. for 1 hour in a sealed box under humid atmosphere. Once incorporation was complete, the wafer arrays were washed with incorporation buffer prior to imaging (see FIG. 11A-11D). The features which are lighting up in channel 1 show incorporation of dGTP nucleotide (see FIG. 11A). Features lighting up in channel 2 show dTTP incorporation (see FIG. 11B), with dATP incorporation in channel 3 (see FIG. 11C) and dCTP incorporation in channel 4 (see FIG. 11D). The barcode region (middle adaptor) of the wafer chip contains an array of sequences with different base combinations, and an incoming synthesis base could be any of the four bases (A, T, G, C) at any specific reason. The images shown in FIG. 11A-11D demonstrate the ability to observe which base extension occurred where on the array, thereby allowing sequencing by synthesis.

In order to do single base primer extension on the inverted wafer chip sequence, a 3' blocked complementary sequence, FC2 having an overhang (3'-ACGTTCGAACGTAGCT-5' (SEQ ID NO: 3)) at 5' position was, hybridized with top adapter of inverted wafer in the same way as mentioned above. Illumina incorporation reaction mixture (400 mL), containing DNA polymerase and fluorophore-labelled reversible terminator dNTPs (all four nucleotides were labeled), was placed on top of the wafer chip which was already hybridized with primer (3' ddc-FC2-overhang). The chip was then incubated at 50° C. for 1 hour in a sealed box under humid atmosphere. Once incorporation was complete, the wafer arrays were washed with incorporation buffer prior to imaging. The features were lighted up only in channel 2 which shows incorporation of dTTP (see FIG. 12B). Since first base in target primer overhang is dATP, the enzyme only incorporated dTTP at the 3' position of the inverted chip. No signal was seen in any other channels (see FIGS. 12A, 12C-12D).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:
(a) providing a substrate with a plurality of branched linkers coupled to said substrate, wherein said substrate comprises controlled pore glass coupled with a plurality of hydroxyalkyl groups, wherein said plurality of hydroxyalkyl groups are coupled to said plurality of branched linkers, wherein each branched linker comprises (i) a first branch comprising a first alkyne and (ii) a second branch;

(b) reacting said second branch with a mixture of a reagent for a first cleavable linker and a capping reagent, thereby producing a first fraction and a second fraction of said second branches of said plurality of branched linkers, wherein each of said first fraction of said second branches comprises said first cleavable linker, and wherein each of said second fraction of said second branches comprises a capping moiety;

(c) coupling said first cleavable linker to a 3' end of a first oligonucleotide;

(d) coupling a 5' end of said first oligonucleotide to a first azide group; and (e) circularizing said first oligonucleotide by reacting said first azide group with a second alkyne, wherein said second alkyne is said first alkyne or a neighboring alkyne;

wherein efficiency of said circularization increases when compared with no said capping moiety on said second fraction of said second branches of said plurality of branched linkers.

2. The method of claim 1, wherein the ratio between said first cleavable linker and said first alkyne is about 5, about 4, about 3, about 2, about 1, about 0.5, about 0.33, about 0.25, about 0.2, or about 0.1.

3. The method of claim 1, further comprising (f) cleaving said first cleavable linker, thereby decoupling said 3' end of said first oligonucleotide from said second branch.

4. The method of claim 3, wherein another second branch comprises a second cleavable linker coupled to a 3' end of a second oligonucleotide, wherein said second oligonucleotide is shorter than said first oligonucleotide, and wherein said cleaving releases said second oligonucleotide from said substrate.

5. A method, comprising:
(a) providing a substrate comprising controlled pore glass;
(b) attaching a plurality of branched linkers to said substrate, wherein said branched linkers comprise (i) a first branch comprising an alkyne and (ii) a second branch;
(c) attaching a cleavable linker to a first group of said second branches;
(d) attaching a capping moiety to a second group of said second branches, wherein said first group of said second branches is different from said second group of said second branches;
(e) synthesizing a first oligonucleotide on said cleavable linker in 3' to 5' orientation, said first oligonucleotide comprising (i) a 3' end coupled to said second branch via said cleavable linker and (ii) a 5' end coupled to an azide group; and
(f) circularizing said first oligonucleotide by reacting said azide group with said alkyne, thereby coupling said 5' end of said first oligonucleotide to one of said first branches.

6. The method of claim 5, wherein the ratio of said first group of said second branches to said second group of said second branches is between about 5:1 to about 1:5.

7. The method of claim 5, wherein said substrate comprises a plurality of hydroxyalkyl groups.

8. The method of claim 5, further comprising (g) cleaving said cleavable linker, thereby de-coupling said 3' end of said first oligonucleotide from said first group of said second branch.

9. The method of claim 8, wherein a second oligonucleotide is attached to a third group of said second branch, wherein said second oligonucleotide lacks a covalent bond to said first branch, wherein said cleaving releases said second oligonucleotide from said substrate.

10. The method of claim 5, wherein said synthesizing comprises photolithographic synthesis.

11. A system, comprising:
(a) a substrate comprising a plurality of hydroxyalkyl groups coupled to controlled pore glass; and
(b) a plurality of branched linkers coupled to said plurality of hydroxyalkyl groups, wherein each said branched linker comprises (i) a first branch comprising a first alkyne and (ii) a second branch, wherein each of a first fraction of said second branches of said plurality of branched linkers comprises a first cleavable linker and each of a second fraction of said second branches of said plurality of branched linkers directly bonds with a capping moiety, wherein said first cleavable linker is coupled to a 3' end of a first oligonucleotide, and wherein a 5' end of said first oligonucleotide is coupled to a first azide group.

12. The system of claim 11, wherein said first azide group reacts with a second alkyne to circularize said first oligonucleotide, wherein said second alkyne is said first alkyne or a neighboring alkyne.

13. The system of claim 11, wherein the ratio between said cleavable linker and said capping moiety is about 10, about 5, about 4, about 3, about 2, about 1, about 0.5, about 0.33, about 0.25, about 0.2, or about 0.1.

14. The system of claim 11, wherein said plurality of branched linkers coupled to said substrate via a first intermediate selected from the group consisting of the structures of

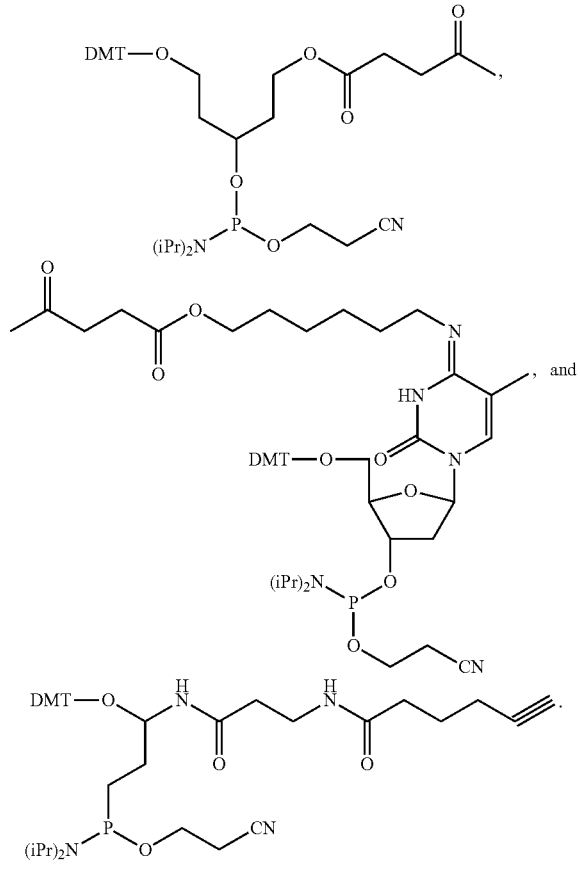

15. The system of claim 11, wherein said first cleavable linker becomes part of said branched linker via a second intermediate selected from the group consisting of the structures of

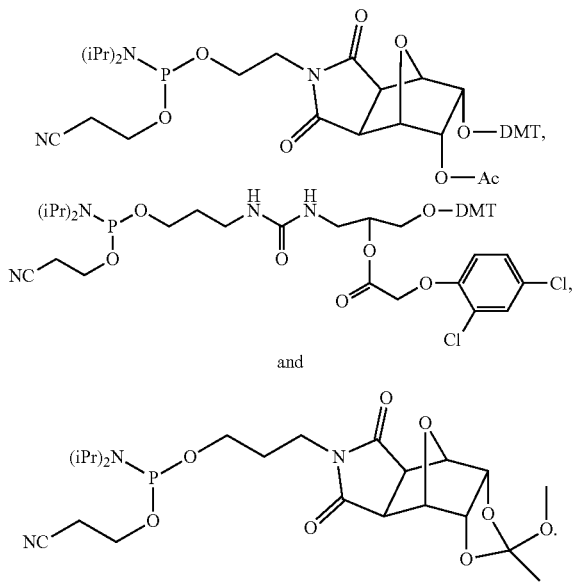

and

16. The system of claim 11, wherein said capping moiety is acyl, dialkoxyphosphoryl, alkyl, alkoxycarbonyl, or dialkyaminocarbonyl.

17. A method, comprising:
(a) providing a substrate with a plurality of branched linkers coupled to said substrate comprising controlled pore glass, wherein each branched linker comprises (i) a first branch comprising a first alkyne and (ii) a second branch;
(b) reacting said plurality of branched linkers with a mixture of a reagent for a cleavable linker and a capping reagent, thereby forming a first fraction and a second fraction of said second branches, wherein each of said first fraction of said second branches of said plurality of branched linkers comprises said cleavable linker coupled to a 3' end of a first oligonucleotide, wherein concurrently each of the second fraction of said second branches of said plurality of branched linkers comprises a capping moiety, and wherein a 5' end of said first oligonucleotide is coupled to an azide group;
(c) reacting said azide group with a second alkyne to circularize said first oligonucleotide, said reaction being catalyzed by a Cu(I) catalyst in a buffer at room temperature, said second alkyne being said first alkyne or a neighboring alkyne; and
(d) cleaving said cleavable linker, thereby inverting said first oligonucleotide.

18. The method of claim 17, wherein said second alkyne is said first alkyne.

19. The method of claim 17, further comprising:
(e) providing a second oligonucleotide complementary to at least part of inverted first oligonucleotide obtained in (d), wherein said second oligonucleotide leaves a 3' overhang after hybridization with said inverted first oligonucleotide; and
(f) extending said second oligonucleotide with a polymerase and fluorescently labeled dNTP, thereby confirming said inversion of said first oligonucleotide.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggctgagtat gtggtctat                                                 19

```
<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgaacgacgc aatagaccac atactcagcc                                          30

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgatgcaag cttgca                                                         16

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(18)
<223> OTHER INFORMATION: a, c, t, g, unknown or other

<400> SEQUENCE: 4
ggctgagtat gtggtcnnt                                                      19

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgaacgacgc aatagaccac atactcagcc                                          30

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(19)
<223> OTHER INFORMATION: a, c, t, g, unknown or other

<400> SEQUENCE: 6
ggctgagtat gtggtctnn                                                      19
```